US012774982B2

(12) United States Patent
Veugelers et al.

(10) Patent No.: US 12,774,982 B2
(45) Date of Patent: Oct. 27, 2026

(54) NANOPORE SYSTEM FOR SENSING USING IDENTIFICATION MOLECULES AND METHOD THEREOF

(71) Applicant: IMEC VZW, Leuven (BE)

(72) Inventors: Mark Veugelers, Merelbeke (BE); Koen Martens, Aalter (BE); Pol Van Dorpe, Spalbeek (BE)

(73) Assignee: IMEC VZW, Leuven (BE)

( * ) Notice: Subject to any disclaimer, the term of this patent is extended or adjusted under 35 U.S.C. 154(b) by 732 days.

(21) Appl. No.: 17/978,595

(22) Filed: Nov. 1, 2022

(65) Prior Publication Data

US 2023/0266265 A1 Aug. 24, 2023

(30) Foreign Application Priority Data

Nov. 4, 2021 (EP) .................................... 21206484

(51) Int. Cl.

| | |
|---|---|
| ***G01N 27/414*** | (2006.01) |
| ***C12Q 1/6825*** | (2018.01) |
| ***G01N 27/327*** | (2006.01) |
| ***G01N 33/487*** | (2006.01) |
| ***G01N 33/543*** | (2006.01) |
| ***G01N 33/68*** | (2006.01) |

(52) U.S. Cl.

CPC ....... *G01N 27/4145* (2013.01); *C12Q 1/6825* (2013.01); *G01N 27/3278* (2013.01); *G01N 27/4146* (2013.01); *G01N 33/48721* (2013.01); *G01N 33/54373* (2013.01); *G01N 33/6803* (2013.01); *C12Q 2600/156* (2013.01); *C12Q 2600/158* (2013.01)

(58) Field of Classification Search

CPC .. G01N 27/4145–4146; G01N 27/3275–3278; G01N 27/48; G01N 33/48721; C12Q 1/6825

See application file for complete search history.

(56) References Cited

U.S. PATENT DOCUMENTS

2007/0190543 A1* 8/2007 Livak .................. C12Q 1/6816 977/924
2016/0069834 A1* 3/2016 Sakata ............... G01N 27/4166 204/403.01

(Continued)

FOREIGN PATENT DOCUMENTS

| | | |
|---|---|---|
| CN | 111489791 A | 8/2020 |
| WO | WO-2007/120265 A3 | 10/2007 |
| WO | WO/2021/171040 A1 | 9/2021 |

OTHER PUBLICATIONS

Ren et al., Nanopore extended field-effect transistor for selective single-molecule biosensing, Nature Communications, 8, 586 (2017) (Year: 2017).*

(Continued)

*Primary Examiner* — James Lin
*Assistant Examiner* — Vivian A Tran
(74) *Attorney, Agent, or Firm* — MOSER TABOADA

(57) ABSTRACT

The current disclosure relates to methods and systems for detecting a target molecule in a sample by using identification molecules linked to assay molecules, wherein the assay molecules bind the target, and where the identification molecules are isolated from the sample and run through a nanopore sensor for detecting the target molecule.

14 Claims, 14 Drawing Sheets

Specification includes a Sequence Listing.

(56) References Cited

U.S. PATENT DOCUMENTS

2018/0164280 A1 6/2018 Ecker et al.
2019/0355442 A1* 11/2019 Merriman .......... G01N 27/4145

OTHER PUBLICATIONS

European Extended Search Report for Application No. 22204657-5 dated Mar. 3, 2023.
Bell, et al., "Digitally encoded DNA nanostructures for multiplexed, single-molecule protein sensing with nanopores", Nature Nanotechnology, vol. 11, Jul. 2016.
Jinglin Kong, et al., "Specific biosensing using DNA aptamers and nanopores", WILEY-VCH, Full Paper, pp. 1-18, A., DOI: 10.1002.
Alfaro, et al., "The emerging landscape of single-molecule protein sequencing technologies", Nature Methods, vol. 18, Jun. 2021, pp. 604-617, https:/doi.org/10.1038/s41592-021-01143-1.
Arun Richard Chandrawekaran et al., "DNA nanoswitch barcodes for multiplexed biomarker profiling", Sep. 22, 2020, pp. 1-12, https:/doi.org/10.1101/2020.09.22.309104.
Nicholas A. W. Bell et al., "Digitally encoded DNA nanostructures for multiplexed, single-molecule protein sensing with nanopores", Nature Nanotechnology, Supplementay Information, 2016, pp. 1-28, DOI:10.1038/NANO.2016.50, www.nature.com/naturenanotechnology.
Nicholas A. W. Bell, et al., "Digitally encoded DNA nanostructures for multiplexed, single-molecule protein sensing with nanopores", Nature Nanotechnology, Apr. 4, 2016, pp. 1-8,, DOI:10.1038/NANO.2016.50, www.nature.com/naturenanotechnology.
Kaikai Chen, et al., "Digital Data Storage Using DNA Nanostructures and Solid-State Nanopores", Nano Letters, Nano Lett. 2019, pp. 1210-1215, pubs.acs.org/NanoLett , DOI: 10.1021/acs.nanolett.8b04715.
Jinglin Kong et al., "Specific Biosensing Using DNA Aptamers and Nanopores", Copyright WILEY-VCH Verlag GmbH & Co., KGaA, 69469 Weinheim, Germany, 2018, Advanced Functinal Materials, Supporting Information, pp. 1-12.
Jinglin Kong, et al., "Quantifying Nanomolar Protein Concentrations Using Designed DNA Carriers and Solid-State Nanopores", NANO Letters, 2016, pp. 3557-3562, 16, 3557-3562, DOI: 10.1021/acs.nanolett.6b00627.
Jasmine Y.Y. Sze, et al., Single molecule multiplexed nanopore protein screening in human serum using aptamer modiled DNA carriers, Nature Communications, DOI: 10.1038/s41467-017-01584-3, 2017, pp. 1-10 www.nature.com/naturecommunications.
He, et al., "Digital immunoassay for biomarker concentration quantification using solid-state nanopores", Nature Communications, 12:5348, pp. 1-11, 2021.
Wei, et al., "Rapid Short-Read Sequencing and Aneuploidy Detection Using MinION Nanopore Technology", Genetics, vol. 202, pp. 37-44, 2015.
Wilson, et al., "High-Fidelity Nanopore Sequencing of Ultra-Short DNA Targets", Analytical Chemistry, 91(10): 6783-6789, 2019.
Philpott, et al., "Nanopore sequencing of single-cell transcriptomes with scCOLOR-seq", Nature Biotechnology, 39, pp. 1517-1520, 2021.
Bearden, et al., "Simple and efficient room-temperature release of biotinylated nucleic acids from streptavidin and its application to selective molecular detection", Analytical Chemistry, 91(13):7996-8001, 2019.

* cited by examiner

SEQUENCE LISTING

```
Sequence total quantity: 2
SEQ ID NO: 1             moltype = DNA  length = 10
FEATURE                  Location/Qualifiers
source                   1..10
                         mol_type = other DNA
                         organism = synthetic construct
SEQUENCE: 1
acgttgaatt                                                        10

SEQ ID NO: 2             moltype = DNA  length = 10
FEATURE                  Location/Qualifiers
source                   1..10
                         mol_type = other DNA
                         organism = synthetic construct
SEQUENCE: 2
ccgtgaatcg                                                        10
```

NANOPORE SYSTEM FOR SENSING USING IDENTIFICATION MOLECULES AND METHOD THEREOF

SEQUENCE LISTING

The entire content of a Sequence Listing XML titled "NANOPORE SYSTEM Sequence listing for filing-US.xml" created on May 2, 2023 and having a size of 3 kilobytes, which has been submitted in electronic form in connection with the present application, is hereby incorporated by reference herein in its entirety.

CROSS REFERENCE TO RELATED APPLICATION

This application claims priority to EP patent application, No. 21206484.4 filed on Nov. 4, 2021, incorporated herein by reference in its entirety.

TECHNICAL FIELD

The present disclosure relates to molecule sensing using nanopores. More specifically, the proposed techniques relate to methods for detecting one or more target molecules, such as biomolecules, in a sample by using assay molecules and identification molecules, where the identification molecule is used for identification of the target molecule in the nanopore sensor. The disclosure also relates to nanopores and systems for use thereof.

BACKGROUND

Nanopore sensing has been used for DNA and RNA detection and sequencing for some time, and the interest of the research community has now also turned to nanopore sensing of biomolecules such as proteins and peptides. For developing new therapeutic and diagnostic strategies, the possibility to selectively screen a range of proteins at the single-molecule level in biological fluids is a key feature. Nanopore sensing is attractive as it has the potential to detect multiple distinct types of biomolecules, such as DNA, RNA, and proteins, simultaneously in a complex biological sample, and since it can be integrated into small and portable devices.

N. A. W. Bell et al. Nature nanotechnology 11 (2016): 645-652 discloses a method where the presence of analytes is detected based on engineering a DNA molecule with structural modifications comprising dumbbels, coupling it to an antibody able to bind a target, incubating it with a target to form a complex with the target, which complex may be translocated through a solid-state nanopore.

Patent application WO2021/171040 discloses a similar nanopore sensing method as above, where the readout in the nanopore is of the barcode molecule bound to an assay molecule (binding moiety), and possible also target molecule.

Both these methods has several drawbacks, such as limitations on the type of binding moiety or assay molecule used. Accordingly, enhanced methods for detecting and quantifying molecules using nanopore sensing is needed.

SUMMARY

An object of the present disclosure is to provide methods and systems, which provide alternative and more efficient ways of detecting and quantifying molecules using nanopore sensing, having advantages, such as low cost and/or efficient detection of the presence and/or concentration of the target molecules.

This objective is obtained by a method for detecting one or more target molecules in a sample using a nanopore sensor, the method comprising: providing at least one assay-identification molecule, wherein the assay-identification molecule comprises at least one identification molecule linked to an assay molecule, wherein the identification molecule is able to generate a unique identification signal when translocated through a nanopore sensor and wherein each assay molecule is able to bind to a target molecule of the one or more target molecules, incubating the at least one assay-identification molecule with a sample potentially comprising one or more target molecules, thereby allowing the at least one assay-identification molecule to bind to the one or more target molecules forming at least one target-assay-identification molecule, wherein the correlation between the unique identification signal of the identification molecule (of the assay-identification molecule) and the bound target molecule is known, removing any assay-identification molecule that has not bound any target molecule from the sample, separating the at least one identification molecule from the at least one target-assay-identification molecule, translocating the separated at least one identification molecule through a nanopore sensor to obtain at least one unique identification signal, and detecting any presence of the one or more target molecules in a sample by correlating the obtained at least one unique identification signal to the one or more target molecules.

Further, a system for detecting and/or quantifying a target molecule in a sample is provided, said system comprising: a microfluidic delivery system configured for delivery of the sample (target sample) and at least one assay-identification molecule; a detection unit comprising two reservoirs, where the reservoirs are separated by a nanopore, wherein the microfluidic delivery system is connected with one of the two reservoirs of the detection unit, wherein one of the two reservoirs comprises the identification molecule, the detection unit is configured for detecting any presence of the one or more target molecules in a sample by correlating the obtained at least one unique identification signal to the one or more target molecules; a control unit configured to control the delivery of the molecules of the microfluidic delivery system and the detection unit and providing instructions to the system for executing the steps of incubating the at least one assay-identification molecule with the sample; removing any assay-identification molecule that has not bound any target molecule from the sample; separating the at least one identification molecule from the at least one target-assay-identification molecule; and translocating the separated at least one identification molecule through a nanopore sensor for obtaining the at least one unique identification signal.

Other objects and advantages will become apparent to those skilled in the art from a review of the ensuing detailed description, which proceeds with reference to the following illustrative drawings, and the attendant claims.

BRIEF DESCRIPTION OF THE DRAWINGS

The above, as well as additional objects, features, and advantages of the present inventive concept, will be better understood through the following illustrative and non-limiting detailed description of different embodiments of the present inventive concept, with reference to the appended drawings, wherein:

FIG. 3A is a generic representation and FIG. 3B shows a nanopore FET.

FIG. 12A shows a short barcode and detection of a single DNA target, FIG. 12B shows a variation of the method described in FIG. 12A, whereby a linker hybridisation molecule is used, and FIG. 12C shows another variation of the method described in FIG. 12A, using a "loop-connected" assay-identification molecule.

Figure 1:
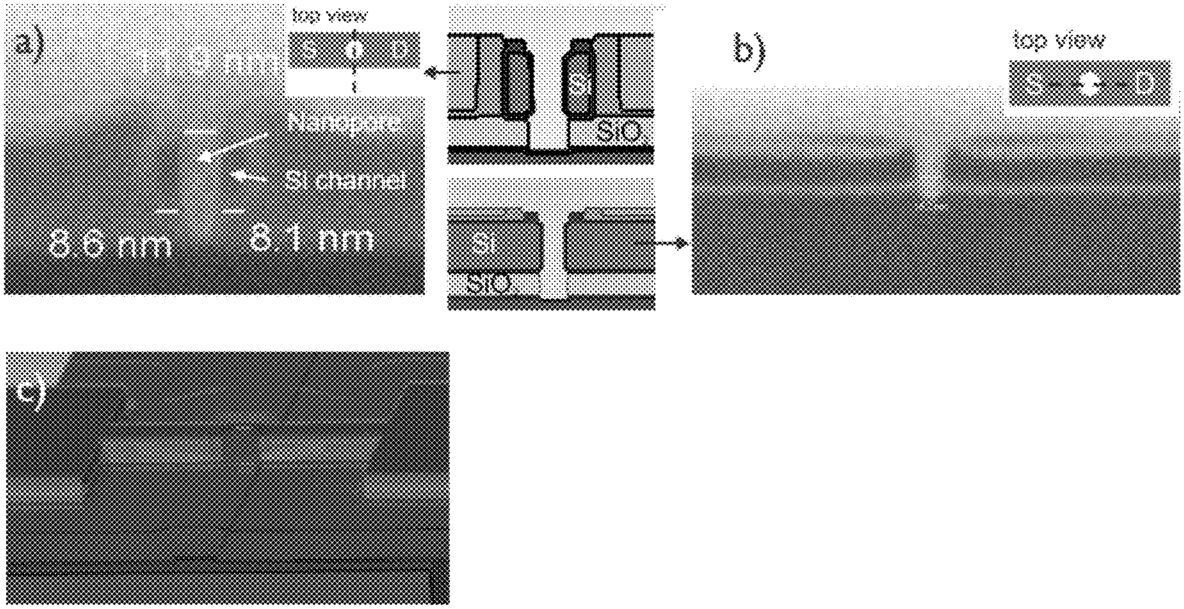
FIG. 1 depicts nanopore sensors, including different cross sections of a nanopore.

The figures are not necessarily to scale, and generally only show parts that are necessary in order to elucidate the inventive concept, wherein other parts may be omitted or merely suggested.

DETAILED DESCRIPTION

Aspects of the present disclosure will be described more fully hereinafter with reference to the accompanying drawings. The system and methods disclosed herein can, however, be realized in many different forms and should not be construed as being limited to the aspects set forth herein. Like numbers in the drawings refer to like elements throughout. For clarity and simplicity, the method will be described in terms of 'steps'. It is emphasized that steps are not necessarily processes that are delimited in time or separate from each other, and more than one 'step' may be performed at the same time in a parallel fashion.

The terminology used herein is for the purpose of describing particular aspects of the disclosure only, and is not intended to limit the disclosure. As used herein, the singular forms "a", "an" and "the" are intended to include the plural forms as well, unless the context clearly indicates otherwise.

In some embodiments a non-limiting term "molecule" as in "target molecule" is used. This refers to any type of analyte that may be detected, identified, and quantified using the methods and system of the invention.

In some embodiments a non-limiting term "biomolecule" is used. The term "biopolymer" may also be used interchangeably. The term "target biomolecule" or "target biopolymer" may be used, and thus refers to the biomolecule/biopolymer that the methods of the invention tries to detect. The target biopolymers or biomolecules herein can be any type of biopolymers, such as polynucleotides, polypeptides, lipids, or polysaccharides, including DNA- or RNA-polymers, peptides, and proteins.

In some embodiments, the generic terminology "identification molecule", is used. The term "barcode molecule" may be used interchangeably when the identification molecule comprises a barcode. An identification molecule or barcode molecule as used herein refers to an engineered elongated molecule that give rise to an identification signal or barcode signal when translocated (read out) on a nanopore sensor. The identification molecule has a "backbone", which may in some embodiments be referred to as "scaffold" or "scaffold backbone", such as a biopolymer backbone or a synthetic non-natural polymer backbone, which comprises one or more modifications, which are added to attain the identification molecule. The biopolymer backbone may be for example DNA, RNA, peptides, saccharides, and lipids, and the synthetic backbones may be for example polyesters, polyamides, rigid-rod polymers and/or modified polymers with carbon linker segments. The backbone may also be an uncharged molecule, for example polyethers, such as polyethylene glycol, PEG, or variants thereof.

Figure 6A:
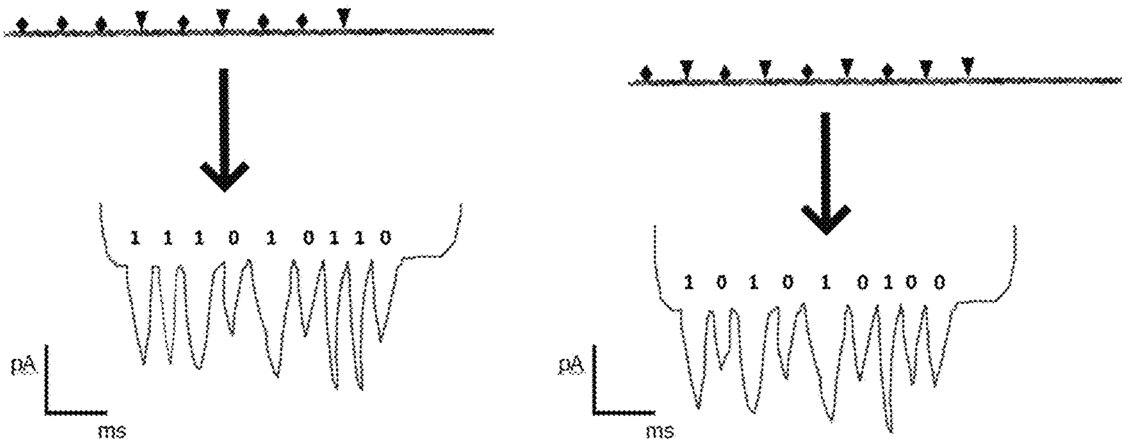
FIG. 6A is an illustration of using two different types of side modifications to give rise to a nanopore readout of peaks, being assigned a unique identification signal/barcode.
Figure 6B:
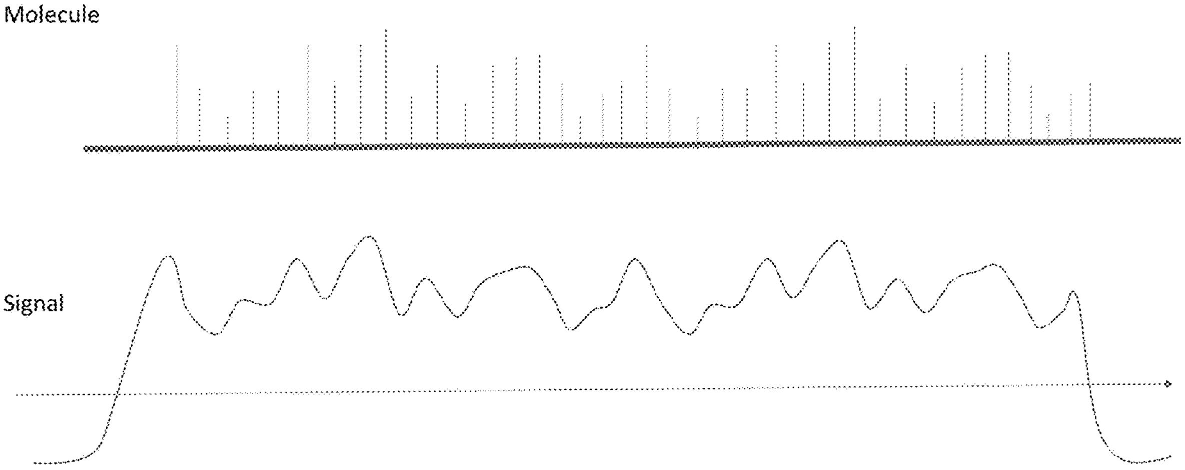
FIG. 6B illustrates a molecule and its resulting signal readout.

The term "modification" or "backbone modification" refers to a modification on the backbone of the identification molecule, which modifications give rise to the unique identification signal or signal change, or signal alternation, when read out in a nanopore sensor. In some aspects a modification on the backbone, e.g. to the backbone itself, is configured to create a unique signal pattern, such as a current peak pattern, when the identification molecule is translocated through the nanopore. The characteristics of the signal pattern can be used as a barcode to identify the target molecule. For example, the change in the signal may be a "raising" or "dropping" signal, or a change in the characteristics of the signal, such as in duration or amplitude of a "raising" or "dropping" signal (peaks). In some embodiments, the changing signal pattern as a whole can be used as a barcode. In some embodiments, a series of changes can be assigned as a value in the barcode. One example is shown in FIG. 6B.

In some embodiments, the modification of the backbone may be by adding a protruding modification to the backbone, in which case the modification/backbone modification may also be referred to as a "side modification", such as a DNA hairpin, which results in a peak signal when the identification molecule is translocated through the nanopore. The modification protrudes from the backbone and may thus be registered by the nanopore sensor, such as a change in current during translocation of the identification molecule. Said modifications may be of different types, referred to as "modification types", where the modification types may be e.g. different DNA hairpins, such as an 8 basepair (8 bp) long DNA hairpin or a 16 bp DNA hairpin. Each modification give rise to a peak when the identification molecule translocates through a nanopore sensor. Different modification types may give rise to different magnitudes of the peaks, and/or a different duration of the peak. The peaks attained in the signal when the identification molecule is translocated through the nanopore is for example due to the change in current during translocation of the identification molecule, thus the "peak" may be a "current peak", but may also be a "voltage peak" (voltage threshold peak), where the nanopore is a voltage divider in the device. Each peak may be assigned an "identification value", which may also be referred to as "value" only, which value may depend on the magnitude and/or duration of the peak (i.e. indirectly based on the modification type). These values be of two or more "types" or "components", such as "0" and "1" being different components. The exact implementation may depend on several factors such as the resolution of the pore. In the case of DNA hairpins, a big difference in hairpin size, as measured by the length in nucleotides protruding from the backbone, will give different peak sizes, e.g. a 8 nucleotide (nt) hairpin will give smaller peaks than a 24 nt hairpin and the difference in size may be sufficient to label all 8 nt hairpins as e.g. 0 and all 24 nt hairpins as 1. The difference in peak size between an 8 nt and 9 nt hairpin may be so small that they will be grouped as having the same size and thus same value. The same applies for other types of modifications. In one example, several magnitudes, such as 1-5 may be assigned the same identification value, while the magnitudes 6-10 may be assigned another value. Also distances between different modifications may be used for assigning a certain identification value, where for example Distance 1 is assigned a value of 0, and Distance 2 is assigned an identification value of 1, for instance, or where for example the presence or absence of modification is assigned a certain identification value. Where the unique signal is a barcode signal, an "identification value" may be referred to as a "barcode value". In one embodiment, two modification types are used, and the barcode value is one of two components, either a "0" or a "1". When having more than two modification types, several modification types may give rise to the same value/component. In some aspects, the magnitude of the peak signal in nanopore sensor is used for assigning the identification/barcode value, where for example there are different magnitudes for "1" and "0", and in other aspects the spacing between the peak signals may be used for assigning the identification/barcode value, where for example the presence of a peak is assigned a "1" and no peak is assigned a "0". All the identification/barcode values of the identification molecule give rise to a pattern, an array of identification/barcode values, which array is referred to as a unique "identification signal" or "barcode signal". In one embodiment, a plurality of modification types, such as three or more, may be used corresponding to a plurality of identification/barcode values, which give rise to more complex identification/barcode signals.

The identification molecules of the present invention may have a backbone that is encoded as a chain structure, with different sizes and or shapes of "blocks", such as origami balls, cubes, or plates. The blocks may have a stable and semi-rigid structure, and may be formed from one or more layers of a nucleic acid, peptide, or protein.

The term "assay molecule" refers to molecules which are designed or intrinsically able to bind target molecules in an assay. This could be any type of bio or synthetic molecule which may be used in an affinity assay of some sort. Each assay molecule is able to specifically bind to a target biomolecule in a sample. The assay molecules may be linked to one or more identification molecules to form an assay-identification molecule. The assay-identification molecule may bind to a target biomolecule when incubated with a sample comprising the target biomolecule, thus forming a target-assay-identification molecule. Assay molecules may be selected from for example proteins, peptides, DNA, RNA, molecularly imprinted polymers, chemical compounds, metal ions, lipids, polysaccharides, vesicles, whole cells, and polystyrene beads. In some embodiments the assay molecule is an antibody, or a binding fragment thereof, such as a single chain variable region fragment, an aptamer or an affimer. It should be noted that the bond between the identification molecule and the assay molecule, and the bond between the assay molecule and the target molecule may be a chemical bond, which may be covalent, ionic and/or metallic.

The nanopore sensor of the present method preferably comprises a solid state nanopore. In some embodiments, the nanopore sensor comprises a nanopore field effect transistor (FET). The nanopore sensor may comprise a first and second electrolyte reservoir, respectively, being separated by a barrier comprising a nanopore. The sensor/system may further comprise electrodes for translocating molecules through the nanopore from the first electrolyte reservoir to the second electrolyte reservoir, wherein at least one of the first and second electrolyte reservoirs comprises the separated identification molecules for detecting the target molecule. The nanopore may have an aperture through which the identification molecule is translocated, where the aperture diameter is linked to the approximate diameter of the identification molecules used. The nanopore may be at least 5, at least 10, at least 30, at least 50, at least 70, at least 100 or at least 130 nm in diameter. It may be less than 200 nm, or less than 150 nm in diameter. As nanopores are not necessarily circular, the term "diameter" of the nanopore refers to the average dimension of the pore. While large pore sizes are not suitable for the detection of single analytes or linear dsDNA carriers, they can be used for larger structures, such as DNA or protein origami structures. By tuning the size of the nanopore to the size of the identification molecule, there is typically less background signal.

In some aspects, the invention relates to a device or system incorporating the nanopore, where a nanopore containing device is configured for performing the methods defined above and below. In some aspects, a system or device of the invention comprises several nanopores, which nanopores may perform simultaneous sensing to attain a high throughput in the system.

In some aspects, a system comprising a microfluidic delivery system is provided, where the microfluidic delivery system deliver different molecules, such as a target sample, an identification molecule, an assay molecule, and an assay-identification molecule. The system may also comprise a detection unit, where the detection unit comprises two reservoirs, where the reservoirs are separated by a nanopore. The microfluidic delivery system may be connected with one of the two reservoirs of the detection unit, wherein one of the two reservoirs comprises the identification molecule that has been separated from the target-assay-identification molecule. The detection unit may detect one or more unique identification signals obtained from the identification molecules as they translocate through the nanopore, and may be configured for detecting any presence of the one or more target molecules in a sample by correlating the obtained at least one unique identification signal to the one or more target molecules. The system may further comprise a control unit, which controls the delivery of the molecules of the microfluidic delivery system, and which controls the detection unit, and provides instructions to the system for performing the methods described above and below, such as incubating the at least one assay-identification molecule with the sample; removing any assay-identification molecule that has not bound any target molecule from the sample; separating the at least one identification molecule from the at least one target-assay-identification molecule; and translocating the separated at least one identification molecule through a nanopore sensor for obtaining the at least one unique identification signal. The incubation step of incubating the at least one assay-identification molecule with the sample may be performed in different location in the microfluidic system, such as pre-mixed in the microfluidic delivery system, as a sperate unit or in one of the reservoirs. The step of removing any non-bound assay-identification molecules may employ a washing or removing mechanism configured for washing/removing the any assay-identification molecule that has not bound any target molecule from the sample to a microfluidic output channel. The step of separating the identification molecule from the complex may employ a separation mechanism configured for separating or isolating the at least one identification molecule being separated from the target-assay-identification molecule by photolysis, heat, pH change, chemical removal or enzymatic removal, by, for example, delivering the chemical/enzyme through at least one microfluidic channel or provide heating/pH modulation from at least one electrode or comprising an illumination source, etc. The identification molecule may be made to translocate between the two reservoirs through the nanopore for example by applying voltages on at least one electrode located in each reservoir. In the event of no target analyte/molecule present in the sample, this may be detected by the detection unit as the unit detects no changes in the signal and brings a negative detection result.

Depending on the resolving power of the nanopore, modifications, such as hairpin DNA structures, need to be spaced sufficiently apart to avoid overlapping peaks. Likewise, the resolving power of the nanopore will determine the minimal length the hairpin DNA extension needs to be to give rise to a peak. A nanopore with high resolving power (such as a nanopore-FET) can still resolve peaks using shorter DNA hairpins which are also more closely spaced next to each other.

The features "nanopore-FET" (NP-FET), or "nanopore-FET device" may be used interchangeably herein and refers to a device comprising a nanopore and a FET sensor, where the FET may be either embedded in the nanopore, or remote, i.e. where an electrode wrapped around the nanopore is connected to a remote gate sensor. Thus, in one embodiment, nanoscale FETs gated by an electrolyte-filled nanopore running through the cannel of the FET, typically a silicone gate, is used in the methods. Alternatively, an electrode is wrapped around the nanopore, which is connected to a remote FET, thus having an extended gate, may be used. In the extended gate device, the silicon in the pore is replaced with an electrode material, wherein the device comprises a remote extended FET, where an electrode wrapped around the nanopore is connected to a remote gate sensor. The electrode material is typically a metal, such as titanium nitride, TiN, ruthenium, Ru or platinum, Pt, which is coupled to the gate of a silicon transistor remote from the pore.

Nanopores are pores of nanometer size that may be created by a pore-forming protein or as a hole in synthetic materials such as silicon or graphene. Nanopores may be organic when formed by pore-forming proteins, or they may be inorganic solid-state nanopores made for example in silicon compound membranes. Nanopores have been shown to function as a single-molecule detector when present in an electrically insulating membrane, where a voltage is applied across the membrane and an ionic current passing through the nanopore is monitored. Cross sections and depictions of nanopores are shown in FIG. 1. The membrane, biological or solid-state, comprising the nanopore is surrounded by an electrolyte solution, where the membrane split the solution into two chambers. An electric field is attained by applying a bias voltage across the membrane, inducing an electric field that drives motion of charged particles (ions). Preferably, all the voltage drop concentrates near and inside the nanopore such that charged particles in the solution only feel a force from the electric field when they are near the pore region, also denoted capture region. Nano-sized polymers, such as DNA or protein having a net charge, will then, if placed in one of the chambers, feel a force from the electric field when near the pore region. Thus, the molecule will be attracted to the pore capture region, enter the nanopore, and inside the nanopore translocate through via a combination of electro-phoretic, electro-osmotic and sometimes thermo-phoretic forces.

For a nanopore of molecular dimensions, passage of molecules, such as DNA, cause interruptions of the current level of the open pore, leading to a signal as the molecule translocates through the pore. Inside the pore the molecule occupies a volume that partially restricts the flow of ions, observed as an ionic current drop. The characteristics of said interruption or disruption of the current may then be used to determine the sequence or identity of the molecule passing through the pore. Based on various factors such as geometry, size and chemical composition, the change in magnitude of the ionic current and the duration of the translocation will vary. Different molecules can then be sensed and potentially be identified based on this modulation in ionic current, which is referred to as nanopore sensing.

Nanopore sequencing is a sequencing technology based on nanopore sensing that may be used for sequencing of DNA and RNA, where a single molecule of DNA or RNA may be sequenced without the need for PCR amplification or chemical labelling. A DNA or RNA sequence may be determined by detecting the bases as the RNA or single stranded DNA (ssDNA) translocates through the pore. Biological nanopores, such as Alpha hemolysin (aHL) and *Mycobacterium smegmatis* porin A (MspA) may be used, and it has been shown that all four bases can be identified using ionic current measured across the aHL pore. Alternatively, solid-state nanopores may be used, which do not incorporate proteins into their systems, but instead uses various metal or metal alloy substrates with nanometer sized pores that allow DNA or RNA to pass through. For example, measurement of electron tunnelling through bases as ssDNA translocates through the nanopore is used as a solid state nanopore sequencing method. Alternatively, DNA sequencing using solid state nanopores and fluorescence may be used, where each base is converted into a characteristic representation of multiple nucleotides which bind to a fluorescent probe strand-forming dsDNA, and each base may be identified by two or four separate fluorescences. The biological nanopores being advantageous due to low translocation velocity, i.e. passing slow enough to be measured, and dimensional reproducibility of the pore size. The solid-state nanopores being advantageous due to stress tolerance to environmental conditions, longevity, and ease of fabrication when mass produced.

Compared to DNA and RNA sensing and sequencing, high-accuracy and low-cost read-out of our protein make-up is not yet feasible. Protein and peptide sensing methods for detection, identification and quantification of proteins and peptides, such as techniques for the detection of protein-type disease markers, typically require expensive facilities and specialized laboratory personnel. Proteomics techniques are centralized in specialized institutes and are carried out with room-filling equipment run by highly trained personnel, with queuing and run-times of multiple days, and its application is currently limited to research purposes. Moreover, the limited throughput, dynamic range, and limit of detection of the current mass spectrometry-based proteomics toolset does not allow to measure the most interesting low abundance proteins in clinical samples. Furthermore, comprehensive single-cell proteomics is not possible. Even though there exist many protein and peptide sensing methods and devices (sensors), the present methods and devices all have drawbacks, such as limited throughput, low accuracy, dynamic range, and cost effectiveness. Thus, enhanced methods and devices for sensing of peptides and proteins are needed.

Moreover, it is not currently possible to determine the complete sequence of any biopolymer (e.g. polynucleotide, polypeptide, polysaccharide) by translocating the biopolymer through a solid-state nanopore or nanochannel. Even though nanopore sensing and sequencing of DNA/RNA polymers is widely employed in the community using biological nanopores, it is still not possible to determine the complete DNA-sequence of a DNA-polymer from the ion current when the unmodified DNA molecule translocates through a solid-state nanopore or nanochannel.

Thus, even though it has not been previously possible to determine a complete DNA-sequence of an unmodified DNA molecule translocating through a solid-state nanopore from the ion current through the nanopore, it is possible to detect the differential electrical signal of different DNA-structures (e.g. DNA hairpins with different hairpin lengths) and regions with different DNA structure (e.g. ssDNA versus ssDNA hybridized with oligos) with solid-state nanopores and nanochannels. The spacing and type of these DNA-structures can be modified/designed such that the electrical signal readout using a solid state nanopore resembles a barcode.

Figure 2A:
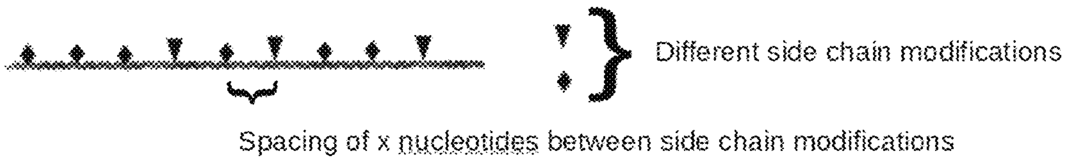
FIG. 2A illustrates a backbone with side chain modifications of different types.
Figure 2B:
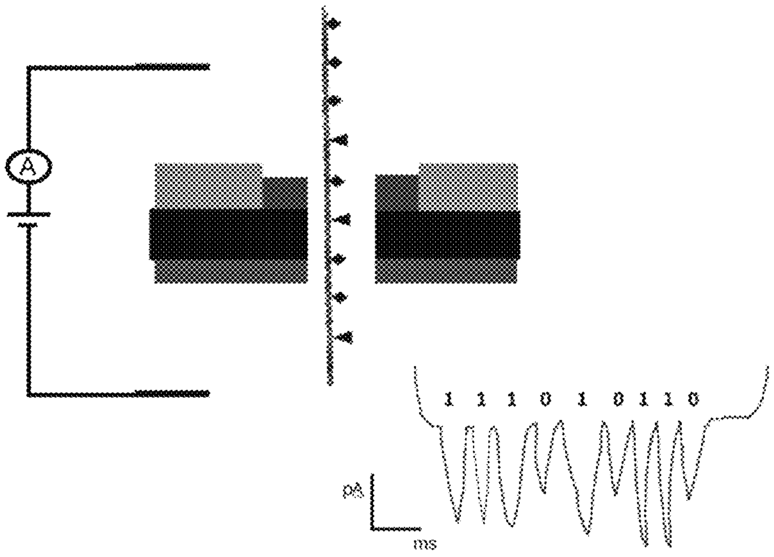
FIG. 2B illustrates a backbone with side modifications passing through a nanopore sensor giving rise to a peak pattern.
Figure 2C:
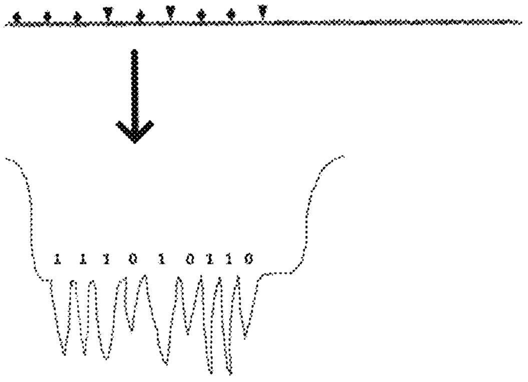
FIG. 2C illustrates that a backbone with modifications give rise to a peak pattern that may be translated into values, which may be represented by zeroes and ones.
Figure 3A:
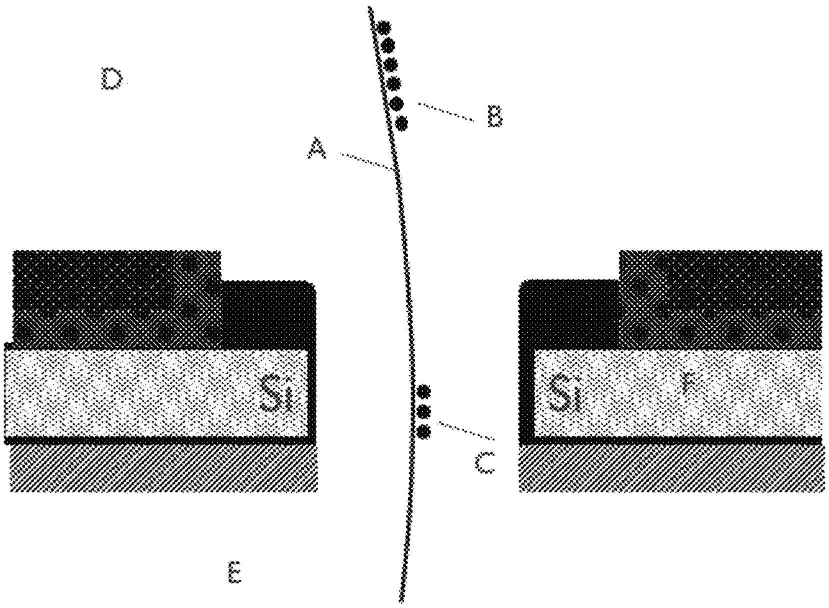
FIGS. 3A and 3B illustrates a dsDNA backbone having modifications thereon passing through a nanopore, where
Figure 3B:
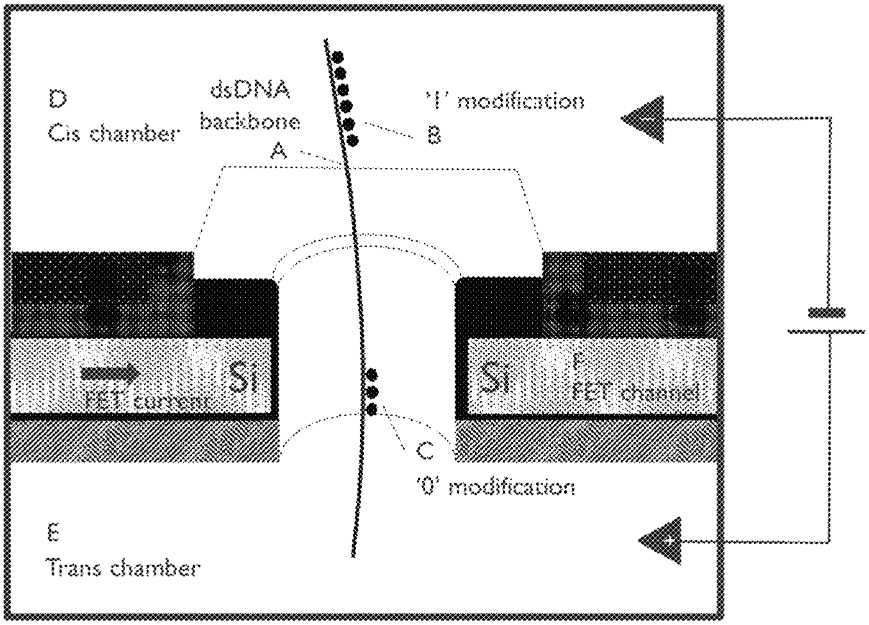

As shown in FIG. 2A, side modifications may be made to the DNA carrier, which side modifications block the current going through the solid-state nanopore as shown in FIG. 2B, e.g., having DNA stick out from the double strand (e.g. by a dumbbel), leading to a peak in the electric signal. By varying the position and type of the dumbbels, one can generate a combination of peaks which constitute a barcode pattern, as also shown in FIG. 2B. FIG. 2C also illustrates the relation between side modifications and the attained peak pattern and resulting identification signal 111010110. One such example is illustrated in FIG. 3. FIGS. 3A and B illustrates a backbone A, such as a double stranded DNA, having thereon modifications B and C, giving rise to values "1" or "0", respectively, passing through a nanopore sensor with chambers D and E.

Figure 4A:
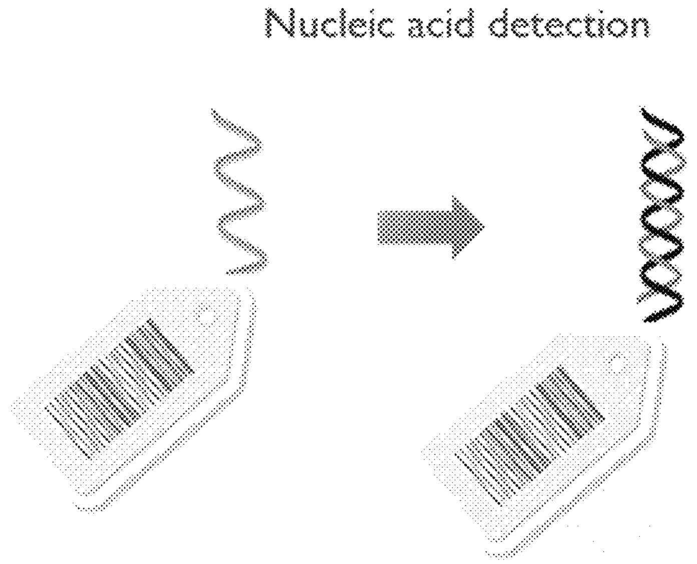
FIG. 4A illustrates barcodes linked to a nucleic acid assay molecule enabling detection of nucleic acid target molecules.
Figure 4B:
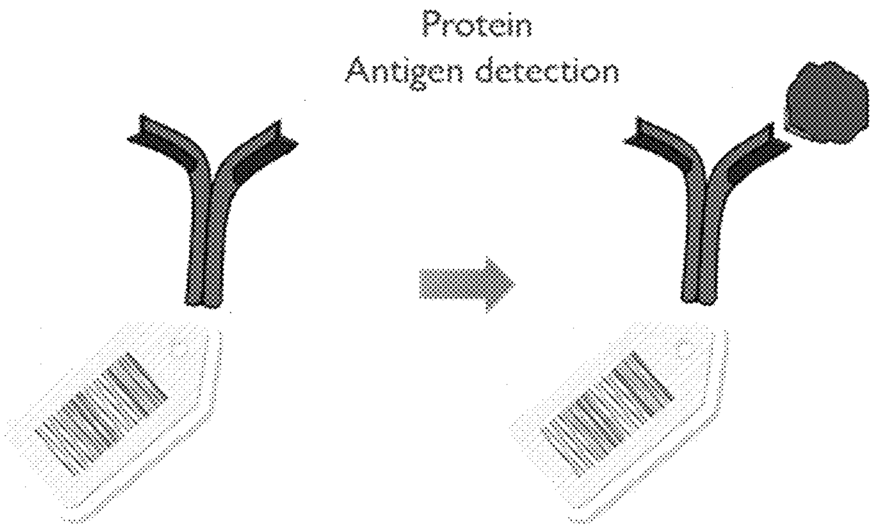
FIG. 4B illustrates barcodes linked to an antibody assay molecule enabling detection of protein antigen.
Figure 5A:
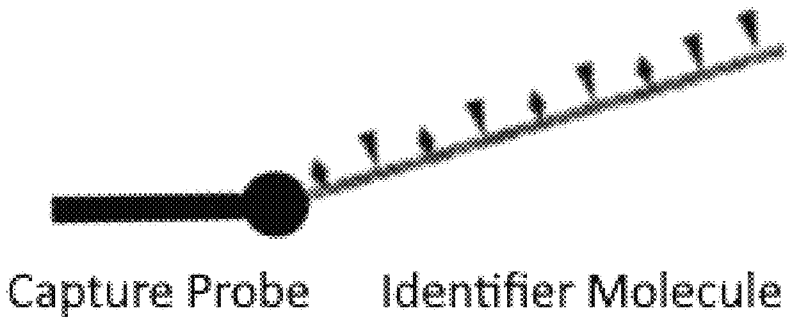
FIG. 5A illustrates a DNA hairpin structure is attached to an RNA capture molecule, and FIG. 5B a photocleavable DNA hairpin structure is attached to an antibody capture molecule.
Figure 5B:

Thus, barcodes may be used both for nucleic acid detection, as well as protein detection, as shown in FIGS. 4A and 4B. A DNA hairpin structure (identification molecule) may be attached to an RNA capture molecule (assay molecule), allowing hybridisation to a target RNA in a sample, as shown in FIG. 5A, and a photocleavable DNA hairpin structure (identification molecule) may be attached to a protein capture molecule (antibody-assay molecule) allowing binding to the target protein, as illustrated in FIG. 5B. After photocleavage, the hairpin structure is released allowing readout of the barcode in a solid-state nanopore platform. Using a strategy similar to the nCounter technology developed by the company Nanostring, one can perform gene expression analysis by reading out the hairpin barcodes specific for each capture probe. An example of using two different types of modifications (hairpins) with a certain spacing to give rise to a nanopore readout of peaks, which may be assigned certain values (0 or 1), giving rise to a unique signal is illustrated in FIG. 6A.

In order to provide enhanced sensing methods which avoids drawbacks of the prior art, it has been found by the current inventors that one can allow indirect identification of target biopolymers and biomolecules by only detecting the peak pattern, resembling a barcode from an identification molecule, which has been split from the target biomolecule, where such a split can be performed in various ways (chemically, enzymatically, photolysis etc.). In one example one may use DNA-structures, which give rise to current peak patterns upon nanopore translocation, to design nanopore-readable barcodes as identification molecules. These DNA-structures can be chemically coupled to biomolecules such as DNA, RNA, proteins, peptides, carbohydrates, etc., thereby tagging these biomolecules with a nanopore-readable barcode and allowing indirect identification of these biomolecules, or specific parts of these biomolecules (e.g. a specific DNA/peptide/saccharide sequence), in a sample by separating the identification molecule from the target molecule and translocating the identification molecule only through a nanopore, hence enabling identification of the specific barcode linked to the biomolecule and thus the presence of the biomolecule or a specific part of a biomolecule.

Thus, the assay/methods of the present disclosure has several advantages over the prior art, such as that any antibody-antigen interaction can be analysed in a single-molecule immunoassay, enabling detection of any protein for which an antibody exists. Further, the identification molecules, such as DNA-barcodes, can be coupled to single-cell identifiers, enabling single-cell protein analysis. As the DNA-barcode is separated from the assay and used as a readout of the assay ("separate-from-assay"), enabling much more types of assays.

It has now been realized by the current inventors that by using an identification molecule bound to an assay molecule for detecting the presence (or absence) of a target molecule in an assay, where the identification molecule is separated and read through the nanopore, the detections may be enhanced, both in terms of specificity and multiplexing possibilities. Identification of a specific identification molecule in the nanopore may be correlated to a presence of the target in a sample being used in the assay. In some aspects, the identification molecule in itself may be an identifier, such as the length of it may be correlated to the unique identity. In some aspects, it may carry information, such as modifications, which may be detected in the nanopore as a peak pattern, and assigned identification values, such as barcode values. It should be noted that the "barcode molecules" and "barcode values" of the invention differs from the typical DNA barcode in which the barcode is in the sequence of nucleobases. The unique identity may also be based on transition time between the side modification in the nanopore sensor. If no target molecules are present, then no assay molecules will be bound when incubated with the target sample, and hence no identification molecules will be present.

Accordingly, it has been realized that different bits can be used as "barcodes" (identification signals/sequences) for identification, using identification molecules comprising side modifications, e.g. a DNA hairpin structure which gives a solid-state nanopore readout as 1001101110 can in fact be used as a barcode sequence which is different from a DNA-hairpin structure which gives a nanopore readout as 1111101110, hence a different barcode sequence (array/sequence of identification values), which is the unique identification signal.

In the field of molecular biology, DNA-sequence based barcodes (e.g. a 10-nucleotide barcode sequence can be: barcode 1: ACGTTGAATT (SEQ ID NO:1), barcode 2: CCGTGAATCG (SEQ ID NO:2)) are frequently used to identify biomolecules. Compared to the identification molecules of the present invention, these DNA-sequence based barcodes are not distinguishable by measuring ion currents upon translocation of DNA-sequence based barcodes through solid-state nanopores, while their use in biological, protein-based nanopores is limited due to the current high error rates of DNA sequencing in protein-based nanopores, thus requiring long DNA sequences to take sequencing errors into account.

Vice versa: certain DNA hairpin structure based barcodes cannot (or at least with very difficult efforts) be sequenced using current DNA-sequencing technologies (be it Illumina sequencing or Oxford Nanopore sequencing).

By transforming a DNA-sequence based barcode into a DNA hairpin structure based barcode, it becomes possible to use solid-state based nanopores to perform the same type of assays as are possible using DNA-sequence based barcodes on current DNA-sequencing platforms. This includes a broad application space such as the use of DNA-encoded chemical libraries, whereby chemical molecules can be tagged with DNA hairpin barcodes. Additional applications are "Microscopy by DNA-sequencing" also called DNA-sequencing-microscopy whereby the physical association and crosslinking of proximal DNA hairpin barcode molecule tagged assay molecules followed by readout in a solid-state nanopore enables to deduce the spatial organization of the assay molecules.

One is not limited to using hairpin DNA sequences as backbone/side modifications of a DNA backbone to design nanopore readable identification molecules/barcodes: any bulky DNA-structure (cruciform DNA, DNA-origami, quadruplex DNA) or DNA-modification (biotin, oligo, peptide, PNA) or different DNA structure (e.g. ssDNA versus ssDNA hybridised with oligos) and combinations of the above can be used to design a solid-state nanopore-readable identification signal.

Readout of DNA-structure based identification molecules/barcodes on a solid-state nanopore has the advantage compared to DNA sequence based barcode readouts of very low assay cost, and extremely high and fast throughput per assay. Since very long DNA molecules can be translocated through solid-state nanopores, and since it is the distance between DNA hairpins or DNA structures which determines the array of values of the identification molecule (identification signal/barcode signal), one can use very short identification signals (e.g. 01) in addition to extremely long identification signals (1010110101 . . . ). One can use different identification systems: e.g. the identification signal can be varied in length (e.g. a barcode with 2 components here indicated with 0 and 1, which can give identification signals such as 0011010 or 1110000000), and one can also design complex barcodes whereby multiple components can be used (leading to barcodes of sequence $0a^2$&, whereby 0, a, $^2$, & are different DNA-structures.

In the present disclosure identification molecules are used for identifying a target in a sample. In some aspects, these identification molecules are designed as nanopore-readable barcodes, where the identification molecules are coupled to assay molecules, such as antibodies, for detecting target biomolecules in a sample, whereby the biomolecules may be indirectly identified and quantified by separating the identification/barcode molecules from the assay-target complex and translocating the identification molecules only through a nanopore, hence enabling identification of the specific barcode linked to the biomolecule and thus the presence of the biomolecule or a specific part of a biomolecule. By measuring the quantity (number) of translocated identification molecules relating to a specific biomolecule, a quantity or concentration may be determined, such as an absolute concentration or a relative concentration to another measured biomolecule in said sample. The quantification may be made by counting the number of unique signals attained, which may be correlated to the concentration of the target sample. In some aspects, counting of the barcodes indicates the concentration of the target biomolecules as in a "one barcode-one target molecule" scenario.

The structures used as identification molecules (barcode molecules) in the present disclosure need not only be DNA-structures, but may also comprise any type of backbone to which backbone/side modifications are added, such that these modifications result in a barcode signal when read out in a solid state nanopore, or possibly very large biological nanopore. The backbone may be any linear structure, typically a polymer, which can be used to imprint on it backbone structures (backbone/side modifications) such that upon nanopore translocation, a barcode-like signal, a unique identification signal that comprises an array/sequence of identification values, is observed. Spherical structures (e.g. nanoparticles) or non-linear structures would be limited in their potential to be used for generating a large number of barcodes (unless linked together to form a linear chain), but any type of linear structure would be possible to use if possible to comprise said backbone structures. In some embodiments, the backbone is generated from a charged molecule, such as biopolymers and synthetic polymers. Alternatively, the backbone is generated from an uncharged molecule, for example polyether, such as polyethylene glycol (PEG), or variants thereof. Alternatively, structures such as nanotubes or nanowires can be used.

In some embodiments, the backbone is a biopolymer backbone, such as RNA-, peptide- or saccharide biopolymer backbone, to which one or more backbone or side modification is added, such that these modifications result in a barcode signal in a solid state nanopore, or possibly very large biological nanopore. In other embodiments, the backbone is a synthetic polymer backbone, such as polyesters, polyamides, rigid-rod polymers, and modified polymers with carbon linker segments. In a preferred embodiment, the backbone comprising modifications is a DNA backbone comprising modifications in the form of DNA hairpin structures and DNA dumbbells.

These identification molecules/barcode molecules or side modifications thereof (barcode structures), can then be chemically coupled to another biopolymer such that the biopolymer becomes barcoded, and after assaying and removal of the identification molecule, the current peak pattern of the identification molecule/barcode structures can be read using a solid state nanopore.

Accordingly, the present invention relates to providing, such as generating, an identification molecule comprising a backbone with modifications, which, when translocated through a nanopore sensor give rise to an identification signal, said signal either read directly from the identification molecule, or by assigning values to the peaks attained from the modifications of the identification molecule. The backbone or side modifications may be of multiple modification types, which generate different peaks when read out on a nanopore sensor due to the different impacts on the electrical field. Each peak may be assigned am identification value, such as when using two modification types the identification values may be binary barcode values of "0" or "1", and the complete readout of the identification values of the multiple modifications and corresponding peaks of the identification molecule is referred to as an identification signal, such as 001, 101, or 111 for a three peak readout. Thus, all the identification values of the identification molecule give an array or sequence of identification values in the order of which each peak is attained when the identification molecule translocates through the nanopore, which array/sequence is the identification signal. Accordingly, when using two modification types having identification values of 0 or 1, the identification signal will be a binary signal of zeroes and ones corresponding to the backbone modifications of the identification molecule, where the assignment of identification values for the peaks are predetermined. Thus, each identification molecule comprise a unique identification signal.

The identification molecules may be linked to assay molecules, thereby forming an assay-identification molecule. Assay molecules of the present disclosure are molecules which bind target molecules in an assay, such as an immunoassay, wherein each type of assay molecule is designed to bind a certain target molecule. The assay molecules may be for example DNA, proteins, peptides or polysaccharides, and the assay molecules may be linked to the identification molecule through a variety of methods such direct conjugation, affinity-based conjugation, hybridization, ionic interaction, or crosslinking, such as crosslinking including click chemistry. Thus, as the assignment of identification values to different peaks is predetermined and accordingly the identification signal of each identification molecule known, and since the linking of a certain (one or more) identification molecule to certain assay molecules binding specific target molecules is also known, one or more identification signals may be correlated to a specific target molecule. Also when the identification molecule is identified using other methods that intrinsic barcodes, the link between the unique identity of the identification molecule and assay molecule, binding a specific target, is known, and may be used for detecting the target upon identifying the identification molecule in the nanopore sensor.

Thus, to be able to detect certain target molecules in a target sample, one may create a number of identification molecules linked to assay molecules, which each bind a target molecule. The "sample" or "target sample" to be analysed may be a biological sample, such as biological fluids, including blood, serum, plasma, saliva and urine, cells, including cell populations and cell cultures, cell digests, and environmental samples, or a non-biological sample, such as waste water, inorganic molecule solutions, etc., where certain assay molecules (e.g. aptamers) may be used, which recognize metal ions, such that the assay identification molecule could be used to measure the concentration of metal ions in a non-biological sample. By incubating the assay-identification molecules with the target sample, binding of some of the assay-identification molecules to target molecules in the sample will occur. By removing, such as washing away, unbound assay-identification molecules from the sample, only the assay-identification molecules which has bound to target molecules and formed target-assay-identification molecules will remain in the sample. By separating the identification molecule from the target-assay-identification molecule in the sample, such as having a photo cleavable identification molecule and cleaving off the identification molecule using photolysis, where the separation may include isolation of the identification molecules by removing the identification molecule from the sample, the identification molecule may be run through a nanopore sensor, where the different types of backbone/side modifications of the identification molecule give rise to a signal or peak pattern, which peak pattern may be translated into an identification/barcode pattern, e.g. by assigning identification values to the respective peaks, wherein the identification pattern (sequence of identification values) is referred to as an identification signal. In some embodiments, the identification signal is based on the size or translocation time/duration of the identification molecule.

Even though the preferred nanopores used in the present disclosure are solid state nanopores, identification molecule/barcode readouts could at least in theory also be done using single-molecule DNA sequencing using biological protein nanopores (Oxford Nanopore). However, due to a combination of high error rates (~90% correctly called bases) and relatively low number of reads (250 million for Oxford nanopore) and since this technology has been optimized (both in regards of sample prep and data-analysis) for reading long DNA sequences (the shortest DNA sequence read on an Oxford Nanopore platform is 434 nucleotides; Wei and Williams, 2016), its use for applications requiring a large number of barcodes is limited. While it is possible to solve some of these issues (e.g. sequencing short fragments after concatermeization and rolling circle amplification as in "High-Fidelity Nanopore Sequencing of Ultra-Short DNA Targets", Wilson et al., 2019, or sequencing barcodes on Oxford Nanopore platform in "Nanopore sequencing of single-cell transcriptomes with scCOLOR-seq, Philpott et al., 2021"), they require complex sample preps or synthesis of unique reagents. Thus, solid state nanopores are preferred.

Several identification molecules may be bound to the same target-assay molecule. Thus, a biomolecule can for example be labelled with multiple DNA-structure barcodes (e.g. one barcode type at either side of the molecule). Multiple labelling per site may be used, i.e. having several modifications at one site of the backbone, such as hairpins sticking out left and right at the same position in the backbone. Also hybrid labelling may be used, i.e. labelling the same site of the backbone with several modifications of different sort, such as hairpin DNA, peptide, sugar etc. One may also use a "barcode in a barcode", where it is possible to design backbones from different building blocks, e.g. DNA-peptide-DNA-peptide. The signal from this type of backbone will show different peaks, i.e. a barcode/signal. By adding side modifications to this backbone (e.g. hairpin DNAs), one generates peaks (and thus an identification signal) on the backbone peaks. Together this allows generation of a signal in a signal (barcode in a barcode) and multidimensional barcodes.

In some aspects, the identification molecule comprise a small fraction at each end that give rise to a predetermined array of values for detecting the orientation of the identification molecule as it translocates through the nanopore, for establishing directionality of the identification molecule as it passes through the nanopore sensor. For example, one may have a "barcode region" in the backbone of the identification molecule. Thus, to allow deduction of the orientation of the molecule translocating through the nanopore, smaller identification molecules or backbone/side modifications may also be attached to the respective sides/ends of the molecule ("left" and "right" side of the molecule, or front/end), said small identification molecules comprising backbone/side modifications which translates into an identification pattern (identification signal) of e.g. 10 modifications each, and where the pattern/signal differs between the "right" and "left" side, and also such that it does not occur in the main identification signal of the target molecule to be detected. The identification molecule can translocate through the nanopore in two directions. For example, if it enters in one direction the signal would be 10001111, the reverse direction will give 11110001. To allow use of a large number of identification molecules, the identification molecule can be labelled at one of the two ends with a specific signal, thereby establishing directionality.

As discussed above, the nanopore is typically a solid state nanopore. In some embodiments, the nanopore may have a field-effect transistor (FET) embedded in the nanopore, i.e. becoming a so called FET nanopore sensor also known as nanopore FET (NPFET). A field-effect transistor is a type of transistor that uses an electric field to control the flow of current in a semiconductor. FETs are devices with three terminals: source, gate, and drain. FETs control the flow of current by the application of a voltage to the gate, which in turn alters the conductivity between the drain and source. The most common type of FET is a MOSFET (metal-oxide-semiconductor field-effect transistor), which utilizes an insulator (typically SiO2) between the gate and the body.

Barcode readout with nanopore FET arrays are very effective, with superior throughput, dynamic range, and multiplexing ability. For multiplexing, longer bar codes create billions of labels while e.g. fluorescent labels are limited to 16. For throughput, nanopore arrays with throughputs up to 1 million molecules/s per pore may be attained, giving rise to a bandwidth advantage (>1 MHz) of NPFET. For dynamic range, it may pick up least abundant species, affecting throughput and single molecule sensitivity.

Figure 7:
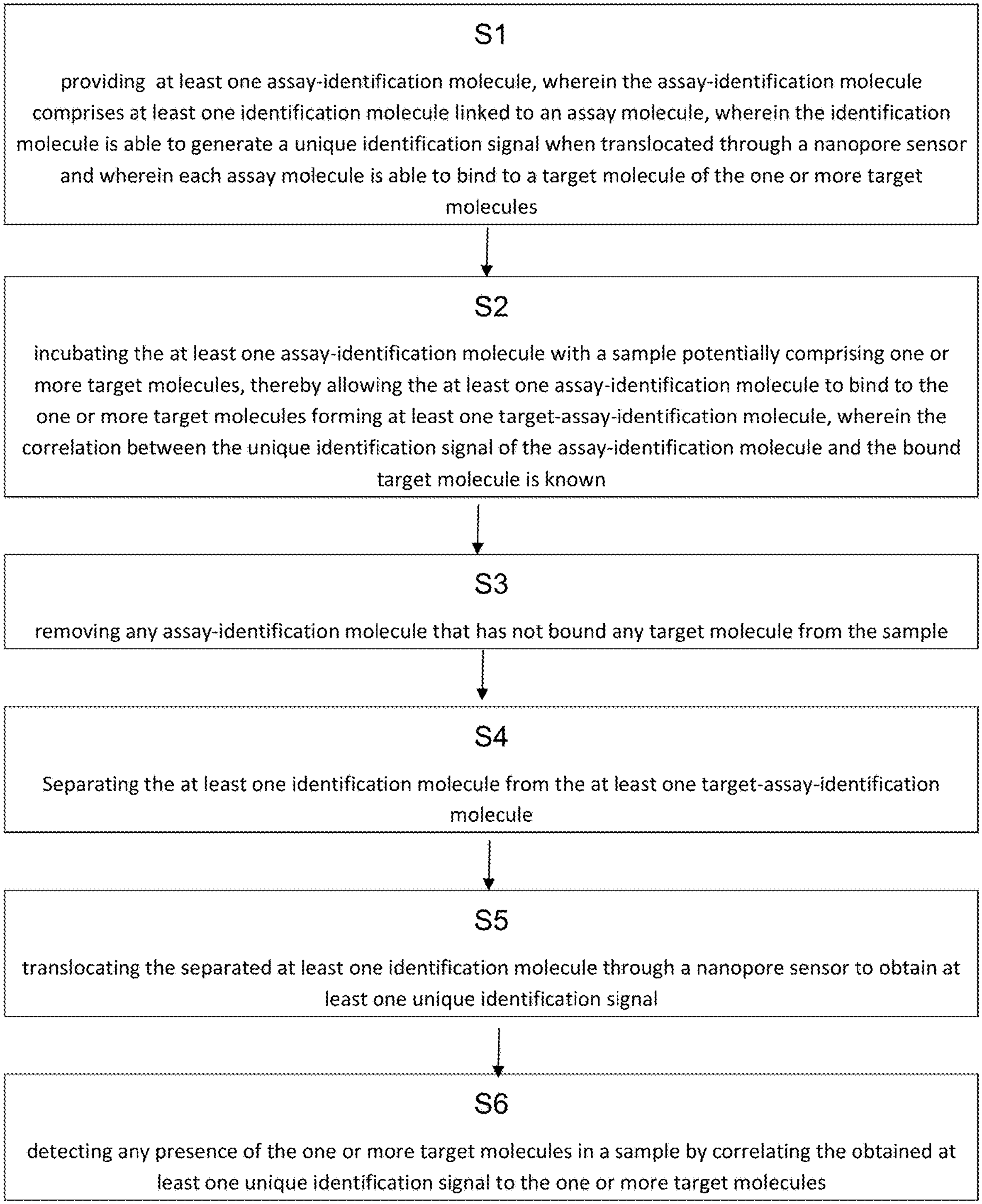
FIG. 7 is a flowchart of an example method of the present disclosure.

The proposed methods will now be described referring to FIG. 7. It should be appreciated that the operations do not need to be performed in order. Furthermore, it should be appreciated that not all of the operations need to be performed. FIG. 7 illustrates a method for detecting, such as identifying the presence of or quantifying, one or more target molecules, such as biomolecules, in a sample using a nanopore sensor, the method comprising providing (S1) at least one assay-identification molecule, wherein the assay-identification molecule comprises at least one identification molecule linked to an assay molecule, wherein the identification molecule is able to generate a unique identification signal when translocated through a nanopore sensor and wherein each assay molecule is able to bind to a target molecule of the one or more target molecules, incubating (S2) the at least one assay-identification molecule with a sample potentially comprising one or more target molecules, thereby allowing the at least one assay-identification molecule to bind to the one or more target molecules forming at least one target-assay-identification molecule, wherein the correlation between the unique identification signal of the assay-identification molecule and the bound target molecule is known, removing (S3) any assay-identification molecule that has not bound any target molecule from the sample, separating (S4) the at least one identification molecule from the at least one target-assay-identification molecule, translocating (S5) the separated at least one identification molecule through a nanopore sensor to obtain at least one unique identification signal, and detecting (S6) any presence of the one or more target molecules in a sample by correlating the obtained at least one unique identification signal to the one or more target molecules.

It should be noted that the in an embodiment, step S5 of translocating (S5) the separated at least one identification molecule through a nanopore sensor to obtain at least one unique identification signal) follows directly the step S4 of separating (S4) the at least one identification molecule from the at least one target-assay-identification molecule. Thus, no modification is made to the barcode after S4 and before S5, and hence only the barcode is translocated and read in the nanopore.

In some embodiments, the identification molecule may comprise further active sites, hence enabling an embodiment with further modification(s) and/or using single stranded DNA as an 'incomplete identification molecule'. In these embodiments, and additional step (S3B) can be added after step S3 (which is then referred to as step S3A), where labels (or additional labels) can be bound/attached to the backbone on these active sites. Hence, it is also possible to add the labels (or additional labels) of the identification molecule at a later stage. Initially, the identification molecule may be a dsDNA with built-in reaction sites for the labels, for example. In that case, the labels can be added later, such as near the end of the procedure. Potential issues with having an imperfect labelling procedure, as not all sites will be labelled, could be addressed using error correction coding. Thus, between the step S3 (removing (S3/S3A) any assay-identification molecule that has not bound any target molecule from the sample) and S4 (separating (S4) the at least one identification molecule from the at least one target-assay-identification molecule), a further step of "attaching (S3B) one or more labels to one or more active sites on the identification molecule" may be present. In the drawings and specification, there have been disclosed exemplary aspects of the disclosure. However, many variations and modifications can be made to these aspects without substantially departing from the principles of the present disclosure. Thus, the disclosure should be regarded as illustrative rather than restrictive, and not as being limited to the particular aspects discussed above. Accordingly, although specific terms are employed, they are used in a generic and descriptive sense only and not for purposes of limitation.

The description of the example embodiments provided herein have been presented for purposes of illustration. The description is not intended to be exhaustive or to limit example embodiments to the precise form disclosed, and modifications and variations are possible in light of the above teachings or may be acquired from practice of various alternatives to the provided embodiments. The examples discussed herein were chosen and described in order to explain the principles and the nature of various example embodiments and its practical application to enable one skilled in the art to utilize the example embodiments in various manners and with various modifications as are suited to the particular use contemplated. The features of the embodiments described herein may be combined in all possible combinations of methods, products, and systems. It should be appreciated that the example embodiments presented herein may be practiced in any combination with each other. The inventive concept has mainly been described above with reference to a few embodiments, however, as is readily appreciated by a person skilled in the art, other embodiments than the ones disclosed above are equally possible within the scope of the inventive concept, as defined by the appended patent claims.

It should be noted that the word "comprising" does not necessarily exclude the presence of other elements or steps than those listed and the words "a" or "an" preceding an element do not exclude the presence of a plurality of such elements. It should further be noted that any reference signs do not limit the scope of the claims, that the example embodiments may be realized in the broadest sense of the claims.

EXAMPLES

Example 1: Analysis of Expression of Cell Surface Proteins Using Solid-State Nanopores This example is described using DNA as a backbone for the identification molecules, and with antibodies as assay molecule. It should be understood that this example may be extrapolated to other types of backbones and assay molecules as described above.

1. Provide/Generate Identification Molecules Comprising "Barcodes"

It should be noted that "carrier molecule" in the present example may refer both to the backbone and to the backbone with modifications, i.e. an identification molecule, where the "barcode structures" are the side modifications to the backbone.

Option A: We start with a carrier molecule/scaffold/backbone: the 7228 nt DNA backbone linearized from M13mp18 ssDNA. This carrier molecule allows to generate 56 barcode structures (hairpins) spaced about 129 nucleotides apart by using binding of 190 oligos of 38 nucleotides. To generate all possible barcode structures (7,20576E+16), more than there are proteins in the human genome, on the M13mp18 ssDNA backbone would require only 316 oligo's.

By using this method, we obtain an identification molecule, which may then be linked to an assay molecule to provide an assay-identification molecule.

Figure 8:
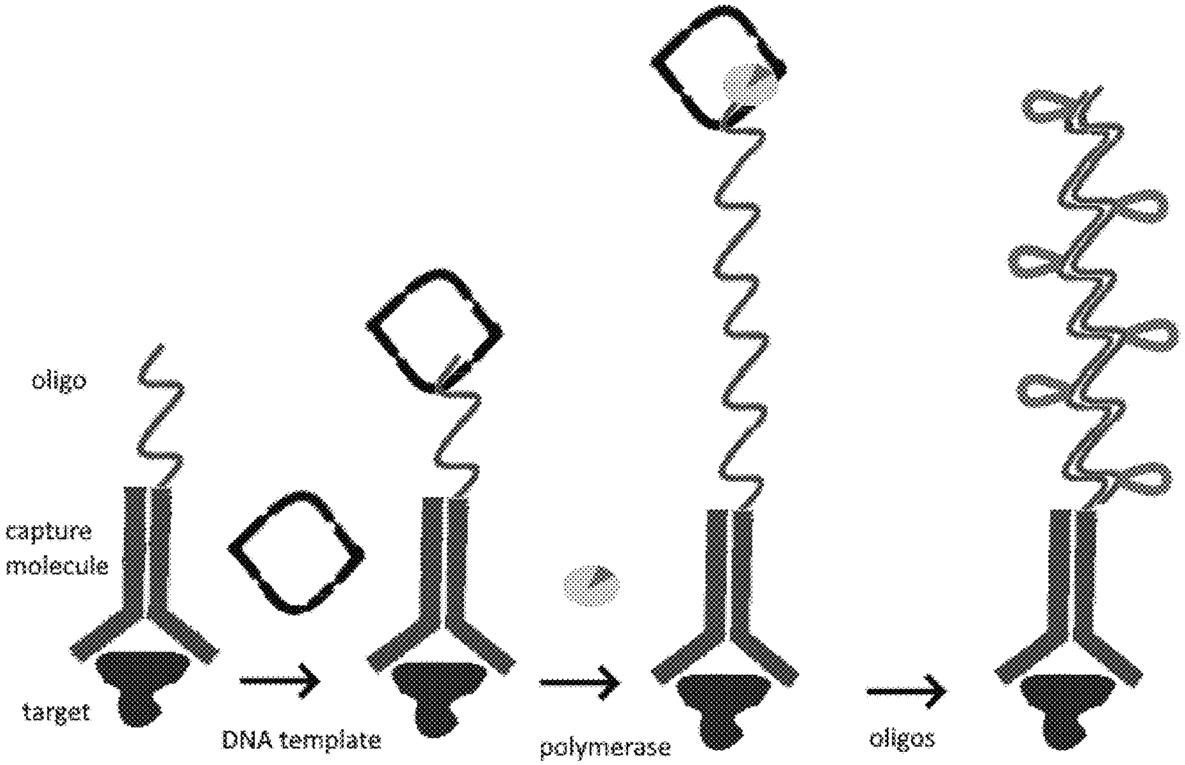
FIG. 8 illustrates the providing of the assay-identification molecule using rolling circle amplification.
Figure 9:
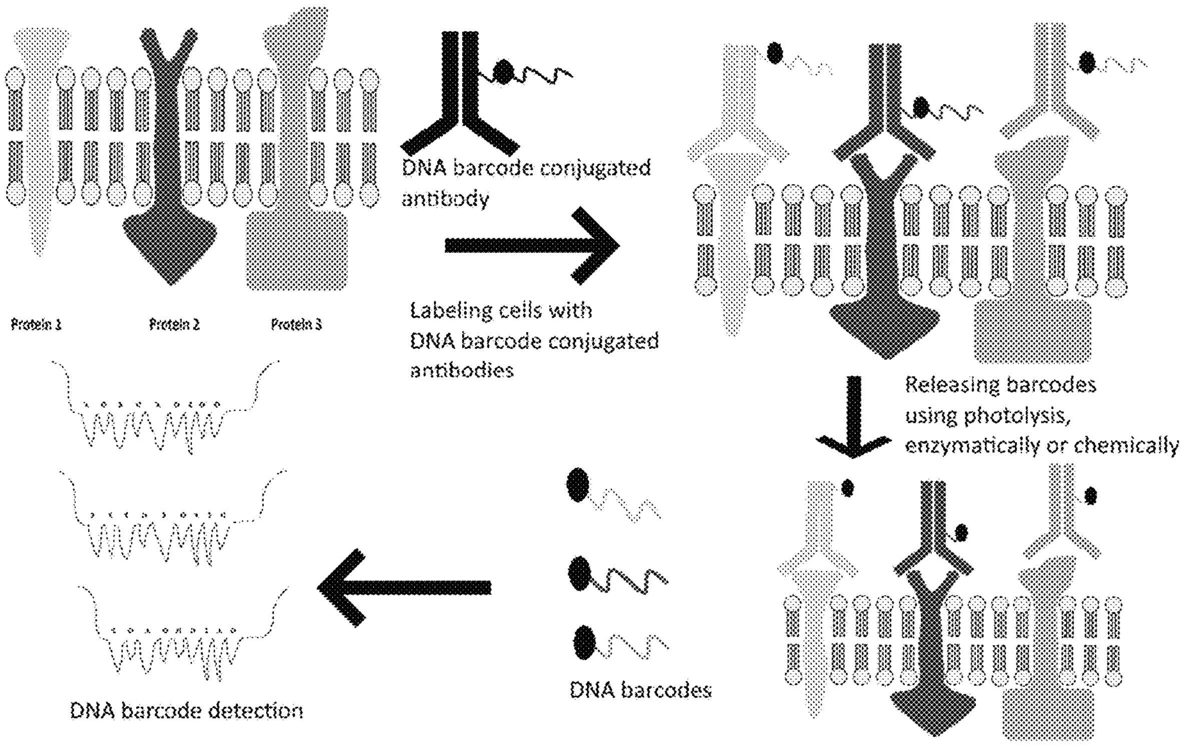
FIG. 9 illustrates an example where cell surface protein expression analysis is performed using assay-identification molecules (barcoded antibodies), using the methods of the invention.

Option B: An alternative would be to use rolling circle amplification to generate a long DNA molecule coupled to the antibody (assay molecule) to which oligo's with barcode structures are hybridized, instead of attaching an assay molecule to the barcode structure (identification molecule), this approach starts with the assay molecule to which a barcode structure is added by DNA hybridization, as illustrated in FIG. 8.

Since we have many barcodes to choose from, there is ample room to allocate some barcodes (modifications giving rise to barcode values), e.g. 10 barcodes on the left side of the molecule, 10 different barcodes values on the right side of the molecule, chosen in such a way that the pattern does not occur in the antibody barcode, to allow deduction of the orientation of the carrier molecule translocating through the nanopore. In each well of a 384-well plate, a set of oligos is combined which bind to the 7228 nt DNA backbone linearized from M13mp18 ssDNA such that a unique identification molecule is obtained in each well.

Multiple plates can be used to scale up the number of generated identification molecules. Alternatively, droplet-based systems may be used to generate and sort billions of identification molecules.

2 Linking the Identification Molecules to Antibodies (Assay Molecules)

This applies to option A above, in which no assay molecule has yet been attached. In option, B, the assay molecules are attached before adding the oligos to create the identification molecules.

In this example, the leftmost oligo, which binds to the carrier molecule/scaffold/backbone, is modified such that it can be linked to an antibody (assay molecule) through a variety of options: ionic, affinity-based conjugation, direct conjugation, or hybridisation.

2.1 Using Existing Oligo-Linked Antibodies

A large set of oligo-nucleotide linked antibodies exist already (Biolegend). By designing the leftmost oligo such that there is a capture overhang with the Biolegend DNA oligo attached to the antibody, the identification molecule can be coupled to the antibody (in fact, the same mechanism is used in CITE-Seq experiments to link the oligo-coupled antibody to bead-linked oligos with complementary overhang). This allows use of the now DNA hairpin labelled Total-seq antibodies in many Total-seq experiments.

A workflow for using Total-seq barcoded antibodies, from labelling cells to solid-state nanopore, comprises the steps of 1) Label cells with Total-seq antibodies, 2) Proteinase K digestions step to attain Total RNA+TotalSeqTag+gDNA, 3) Isolate TotalSeq Antibody Derived Tags, and 4) Release antibody derived tags from beads and nanopore sequencing of barcodes. By designing the rightmost oligo of the identification molecule such that it contains the Totalseq capture region, the barcoder-labelled antibodies (assay-identification molecule) now also become usable for single cell protein expression analysis using 10× genomics.

In current molecular biology workflows, after the release of the antibody derived tags (Step 4), it is required to perform a library prep of the DNA followed by next-generation sequencing. This entire procedure takes several hours for the library prep (which also costs extra money), followed by several hours waiting for the sequencing results and sometimes even weeks of waiting if there is a waiting list at the next-gen sequencing facility. Using nanopore sequencing of identification molecules, both cost and time would be reduced (depending on the pricing of the nanopore sequencing and the cost of generating the identification molecules).

2.2 Using Direct Conjugation

A variety of methods exist for direct conjugation of oligos to antibodies (click chemistry). For example, a UV-photo-cleavable linker can be added. The barcoded antibodies (assay-identification molecules) are incubated with a population of cells. Nonbinding antibodies are washed away. Next, the DNA-structure barcodes from bound antibodies are released by UV exposure and captured from solution using magnetic beads. After release of the DNA, the DNA-structure barcodes are read using a solid state nanopore platform, thereby identifying which proteins were expressed on the cell surface.

3. Nanopore Readout

In an example, the following antibody-barcode complexes (assay-identification molecules) binds (recognizes) the following proteins (target biomolecules).

Antibody 1: barcode 1001110001100>recognizes protein A

Antibody 2: barcode 0110110111011>recognizes protein B

Antibody 3: barcode 1010010101001>recognizes protein C

Etc. . . .

The readout in the nanopore sensor of the barcodes (identification molecules) recognizing protein A, B and C as in the example above may thus be summarized as shown in Table 1.

TABLE 1

| | Antibody barcode | Counts of Barcode Signal in Nanopore |
|---|---|---|
| Protein A | 1001110001100 | 52.220 |
| Protein B | 0110110111011 | 100 |
| Protein C | 1010010101001 | 0 |

Note that since the nanopore measures single molecules, a UMI (unique molecular identifier) is not needed.

Example 2: Cell Surface Protein Expression Analysis Using Barcoded Antibodies In an example of single-molecule immunoassay on solid state nanopore using cleavable identification molecules and methods of the present invention, as shown in FIG. 8, cell surface protein expression analysis using "barcoded antibodies" may be performed.

First, as shown in FIG. 8, DNA-structure barcode labelled antibodies as assay-identification molecules (attached with a photocleavable linker) are incubated with a population of cells (sample with target molecules being proteins expressed on cell surface). Nonbinding antibodies (identification-assay molecule complexes) are washed away. Next, the DNA-structure barcodes (identification molecules) from bound antibodies (identification-assay molecule complexes) are released by UV exposure. The DNA-structure barcodes (identification molecules) are read using a solid state nanopore platform, thereby identifying which proteins were expressed on the cell surface.

Example 3: Protein Expression Analysis Using Barcoded Antibodies

Figure 10A:
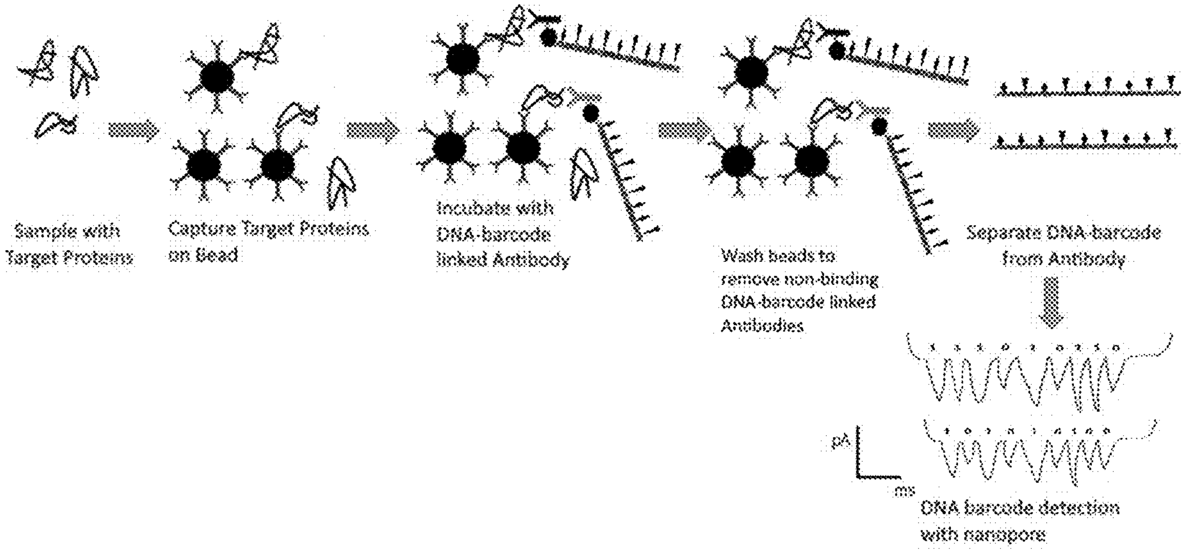
FIG. 10A illustrates an example where protein detection is performed using a sandwich antibody approach and assay-identification molecules (barcoded antibodies), using the methods of the invention.

In another example of single-molecule immunoassay on solid state nanopore using cleavable identification molecules and methods of the present invention, as shown in FIG. 10A, protein expression analysis using a sandwich type of assay with "barcoded antibodies" may be performed.

First, as shown in FIG. 10A, proteins from the sample are incubated with magnetic beads coated with antibodies against the target protein(s). Next, the sample is incubated with DNA-structure barcode labelled antibodies as assay-identification molecules (attached with a photocleavable linker). The beads are collected using a magnet and washed to remove non-bound assay-identification molecules. After the wash, the DNA-structure barcodes (identification molecules) from bound antibodies (identification-assay molecule complexes) are released by UV exposure. The DNA-structure barcodes (identification molecules) are read using a solid state nanopore platform, thereby identifying which proteins were present.

Figure 10B:
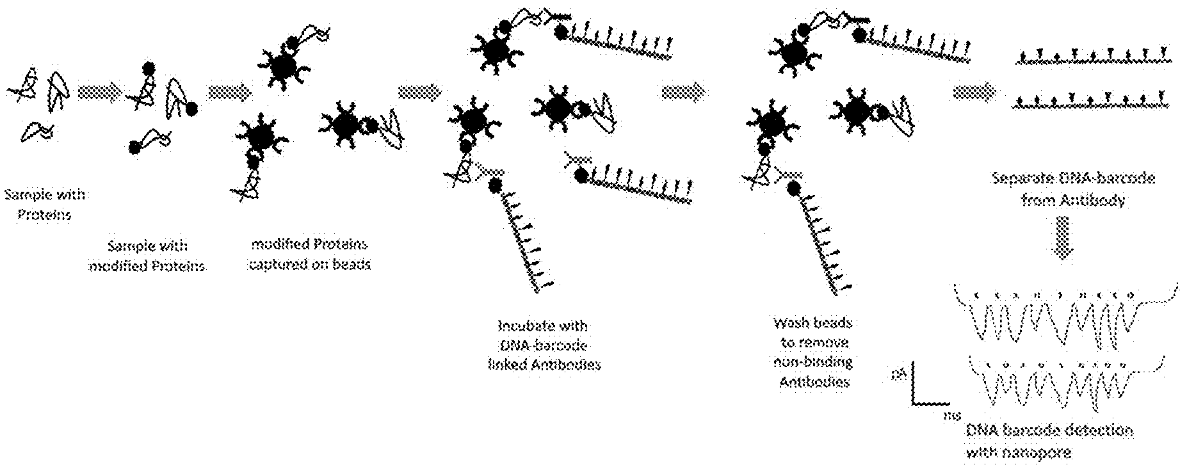
FIG. 10B illustrates an example where protein detection is performed by labelling and capturing proteins on beads and using assay-identification molecules (barcoded antibodies), using the methods of the invention

Second, as shown in FIG. 10B proteins from the sample are labelled e.g. by biotinylation. Next, the sample is incubated Streptavidin-coated magnetic beads allowing capture of all proteins on the beads. This is followed by incubation with DNA-structure barcode labelled antibodies as assay-identification molecules (attached with a photocleavable linker). The beads are collected using a magnet and washed to remove non-bound assay-identification molecules. After the wash, the DNA-structure barcodes (identification molecules) from bound antibodies (identification-assay molecule complexes) are released by UV exposure. The DNA-structure barcodes (identification molecules) are read using a solid state nanopore platform, thereby identifying which proteins were present

Example 4: Gene Expression Analysis Using Barcoded DNA/RNA Capture Molecules

Figure 11:
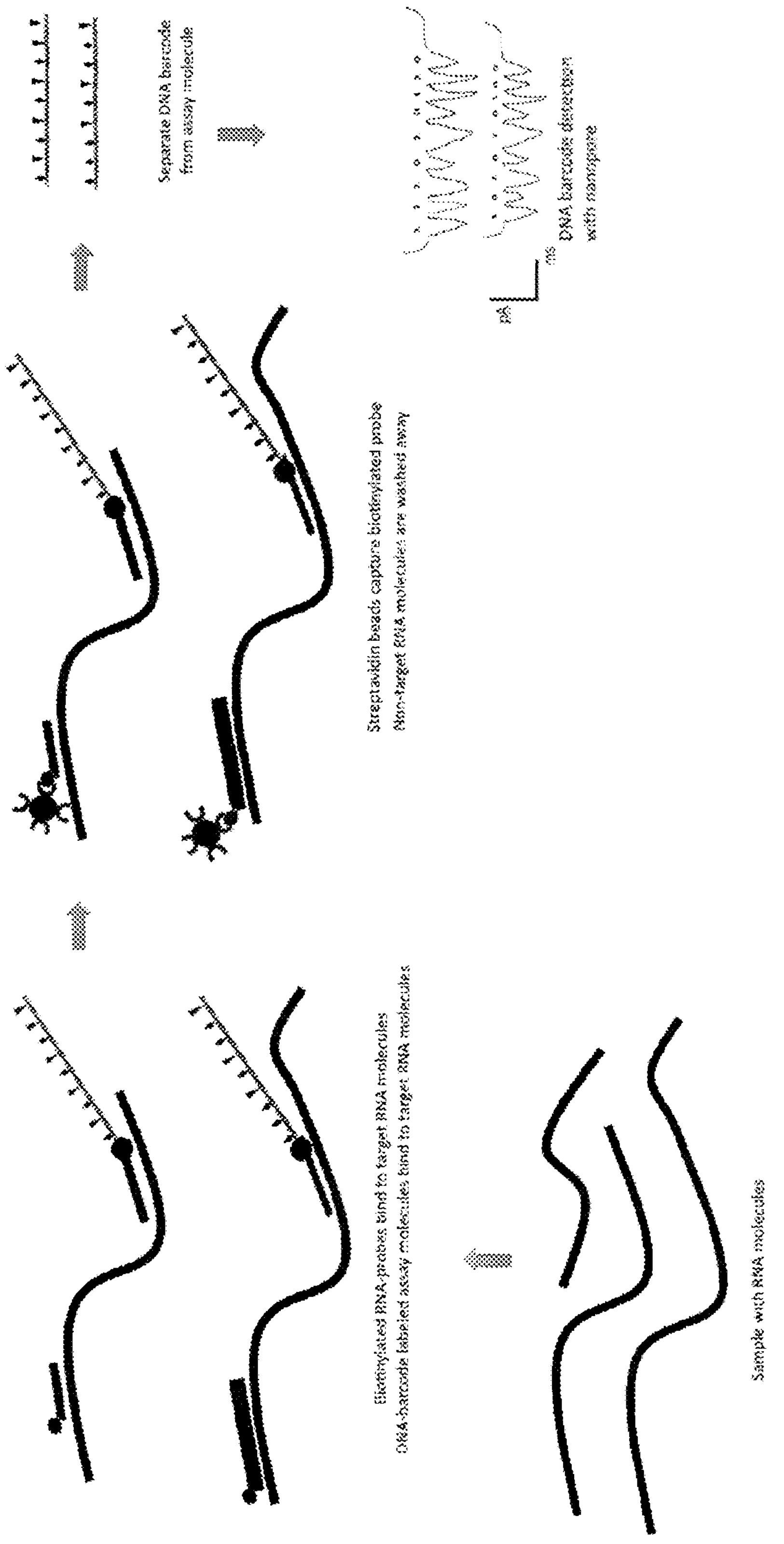
FIG. 11 illustrates an example where gene/mRNA expression analysis is performed using assay-identification molecules (barcoded RNA or DNA molecules), using the methods of the invention.

As shown in FIG. 11, RNA molecules from the sample are incubated with biotinylated RNA-probes or DNA-probes, specific for the target RNA and with DNA barcode labelled assay molecules, whereby the assay molecule is a DNA or RNA molecule which hybridizes specifically to the target RNA. Next, the sample is incubated with magnetic beads coated with streptavidin, thereby capturing the target RNA molecules. The beads are collected using a magnet and washed to remove non-bound RNAs (non-target RNAs). After the wash, the DNA-structure barcodes (identification molecules) are released from the assay molecule by UV exposure. The DNA-structure barcodes (identification molecules) are read using a solid state nanopore platform, thereby identifying which target RNAs were present.

Example 5: DNA Detection/Sensing

For detection of target DNA molecules using assay-identification molecules, hybridisation-based assays can be used.

For hybridisation-based DNA detection, the double stranded (ds) DNA sample is fragmented to uniform size and denatured to generate single stranded (ss) DNA. The target ssDNA is hybridized with biotinylated (B) probes designed to be complementary to the target DNA. DNA targets bound to biotinylated probes are captured on streptavidin (SA) coated magnetic beads (MB). Washing of the beads removes non-target DNA.

Figure 12A:
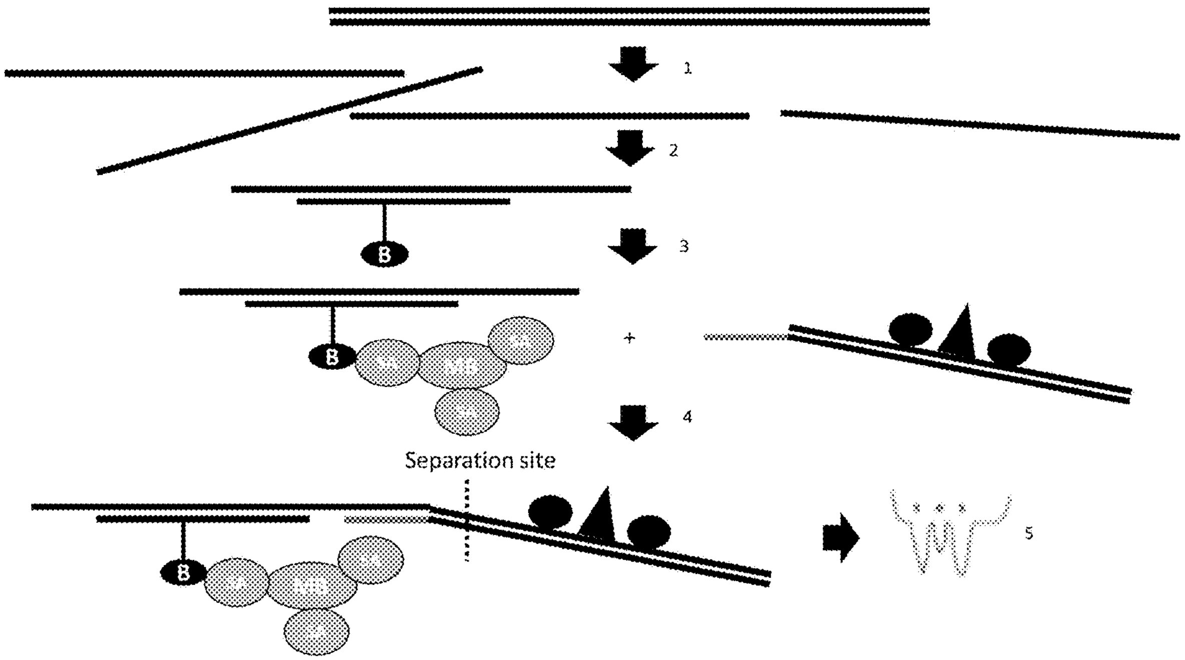
FIGS. 12A-12C illustrate examples of DNA detection/sensing according to an embodiment. More specifically.

The probe-bound target DNA is hybridized on the beads with the assay-identification molecule, indicated in FIG. 12A with the assay part, able to bind to the target DNA, in grey and the identification part in black with different types of DNA side chain modifications (such as e.g. DNA hairpins) indicated by circles and triangles, whereby e.g. a DNA side chain modification represented with a circle would give a signal upon nanopore translocation which is different from the signal upon nanopore translocation of a DNA side chain modification represented with a triangle. These different signals would together result in a barcode signal (e.g. 101), whereby the barcode signal is specific for the assay part of the assay-identification molecule, and thus also the target molecule.

After hybridisation of the assay-identification molecule to the probe-bound target DNA on the streptavidin (SA) coated magnetic beads, non-bound assay-identification molecules are washed away.

The identification molecule is separated from the assay molecule with a restriction enzyme digest or other separation method (UV/chemical, or similar) and the DNA side chain modifications of the identification molecule are read out on a nanopore to generate a barcode signal to allow identification of target DNA.

For simplicity, in FIG. 12A is shown only a short barcode (101) and detection of a single DNA target. For simultaneous detection of multiple DNA targets, one can use assay-identification molecules with several DNA side chain modifications giving rise to a longer barcode, each corresponding to its target. The longer barcodes also allows to have a predetermined array of barcode values for detecting the orientation of the identification molecule as it translocates through the nanopore.

In step 1 of FIG. 12A, for DNA detection, the dsDNA sample is fragmented to uniform size and denatured to ssDNA. In step 2, target ssDNA is hybridized with biotinylated (B) probes. In step 3, DNA targets bound to biotinylated probes are captured on streptavidin (SA) coated magnetic beads (MB). Washing of beads removes non-target DNA. In step 4, the probe-bound target DNA with assay-identification molecule is hybridized on the beads, non-bound assay-identification molecules are washed away. In step 5, the identification molecule is separated with restriction enzyme digest or other separation method (UV/chemical, or similar) and read out DNA side chain modifications, such as hairpins, on nanopore generate a barcode signal to allow identification of target DNA.

Figure 12B:
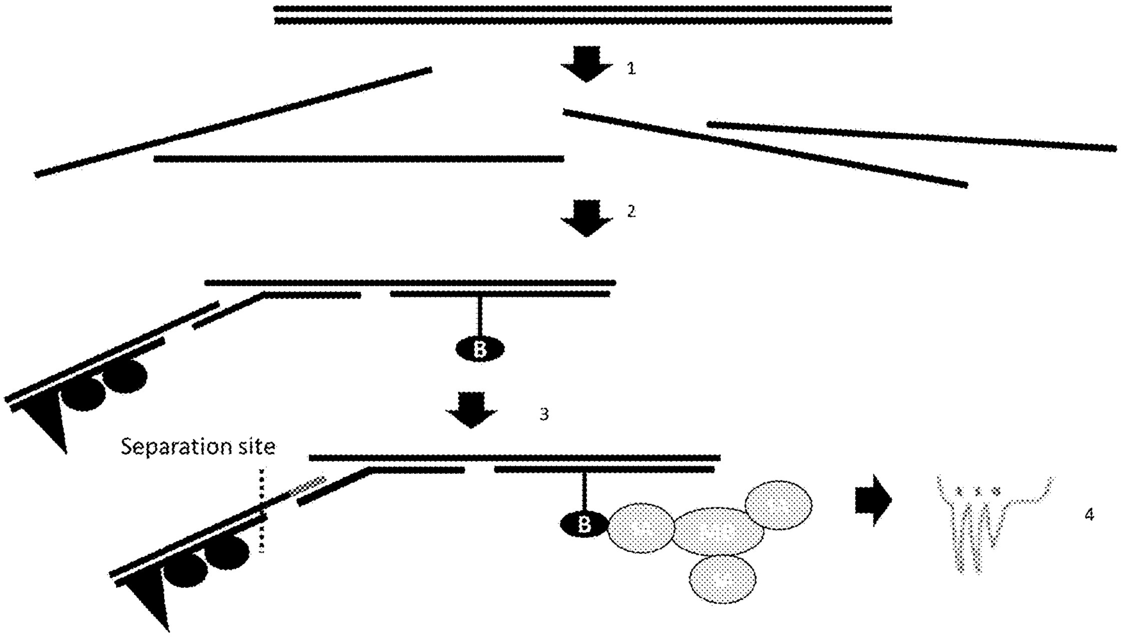

FIG. 12B shows a variation of the method described in FIG. 12A, whereby a linker hybridisation molecule is used. In step 1 of FIG. 12B, for DNA detection, the dsDNA sample is fragmented to uniform size and denatured to ssDNA. In step 2, target ssDNA is hybridized with biotinylated (B) probe, a linker hybridisation molecule and assay-identification molecule. In step 3, DNA targets bound to biotinylated probes are captured on streptavidin (SA) coated magnetic beads (MB). Washing of beads removes non-target DNA. In step 4, the identification molecule is separated with restriction enzyme digest or other separation method (UV/chemical, or similar) and read out DNA side chain modifications, such as hairpins, on nanopore generate a barcode signal to allow identification of target DNA.

Figure 12C:
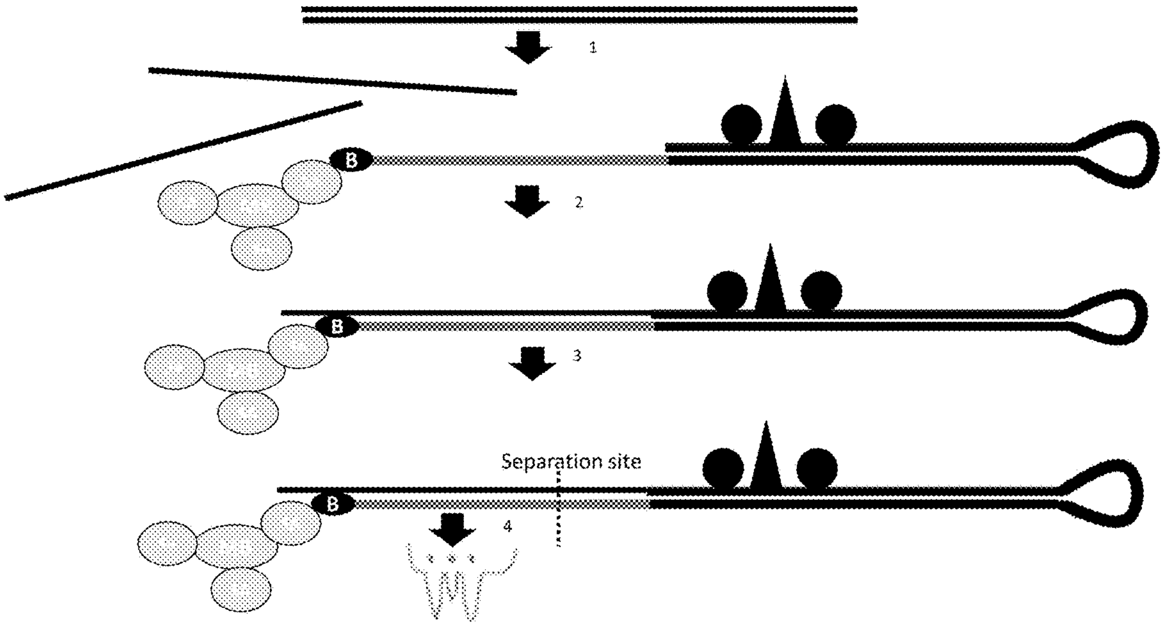

FIG. 12C shows another variation of the method described in FIG. 12A. In this variation a "loop-connected" assay-identification molecule is used, whereby the upper and lower strand of the assay-identification molecule are covalently linked using an internal hairpin. In step 1 of FIG. 12C, the dsDNA is fragmented to uniform size and denatured to ssDNA. In step 2, target ssDNA is hybridized with loop-connected assay-identification molecule with biotin end at the assay molecule side coupled to streptavidin coated magnetic beads. In step 3, DNA targets hybridise to the loop-connected assay-identification molecule with biotin end at the assay molecule side coupled to streptavidin coated magnetic beads. Washing of beads removes non-target DNA. In step 4, the identification molecule is separated with restriction enzyme digest or other separation method (UV/chemical, or similar), the identification molecules are removed, and DNA side chain modifications, such as hairpins, are read out on nanopore to generate a barcode signal to allow identification of target DNA. Assay-identification molecules without bound target are not a target of the restriction enzyme and remain bound to streptavidin coated magnetic beads.

Example 6: SNP Detection

Figure 13:
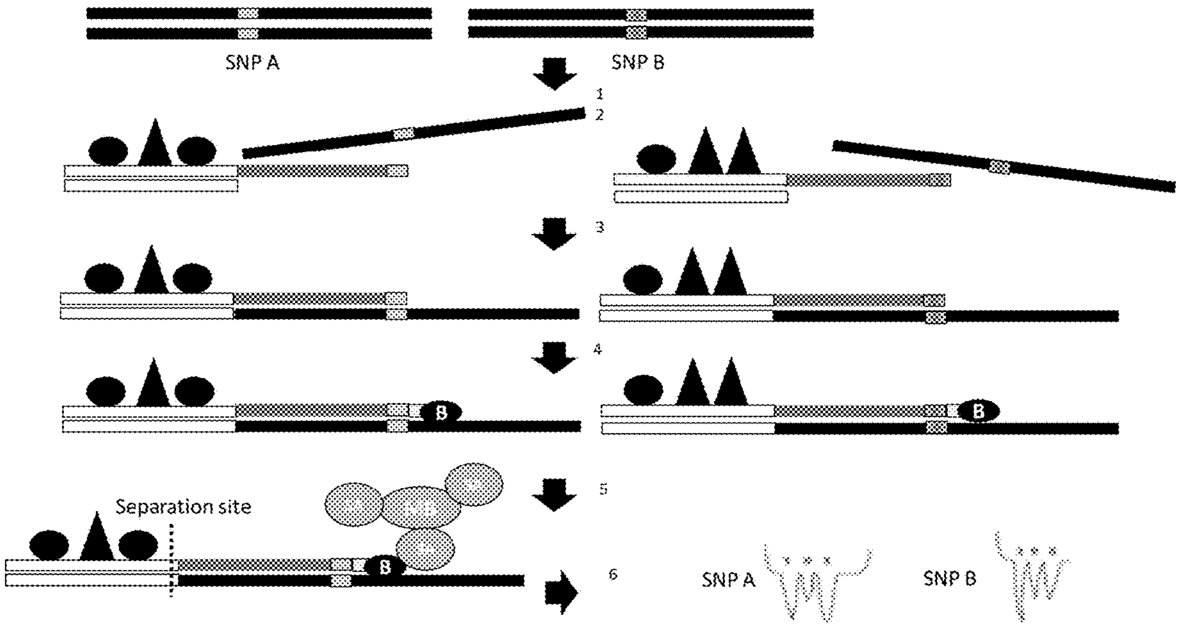
FIG. 13 illustrates an example of SNP detection according to an embodiment.

For SNP detection, the double stranded (ds) DNA sample is fragmented to uniform size and denatured to generate single stranded (ss) DNA, as illustrated in FIG. 13. The target ssDNA is incubated with an assay-identification molecule, whereby the assay molecule part is a complementary DNA-sequence specific for the SNP-variation to be examined. After hybridisation of the assay-identification molecule specific for the SNP-variation with its target, DNA polymerase and biotinylated ddNTPs are added.

If the SNP-variation to be examined was present, the assay-identification molecule will have as its last nucleotide the SNP-variation, allowing DNA polymerase to extend the assay-identification molecule with a single biotinylated ddNTP, whereafter extension will stop. Due to the presence of the biotin group on de incorporated ddNTP, the extended assay-identification molecule will be captured on streptavidin coated magnetic beads.

Next, non-bound assay-identification molecules are washed away. The identification molecule is separated from the assay molecule with a restriction enzyme digest or other separation method (UV/chemical, etc.) and the DNA side chain modifications of the identification molecule are read out on a nanopore to generate a barcode signal to allow identification of target DNA.

For simplicity, we show in FIG. 13 only use of a short barcode (101 or 100) and detection of two SNP target. For simultaneous detection of multiple SNPs, one can use assay-identification molecules with several DNA side chain modifications giving rise to a longer barcode, each corresponding to its target. The longer barcodes also allows to have a predetermined array of barcode values for detecting the orientation of the identification molecule as it translocates through the nanopore.

In step 1 of FIG. 13, the target dsDNA is fragmented to uniform size and denatured to ssDNA. In step 2, target ssDNA is incubated with assay-identification molecule specific for SNP-variation. In step 3, hybridisation of assay-identification molecule specific for SNP-variation with target is performed. In step 4, the hybridized assay-identification molecule is incubated with DNA polymerase and biotinylated ddNTPs. In step 5, is attained capture reaction products on streptavidin coated magnetic beads. Non-bound assay-identification molecules are washed away. In step 6, the identification molecule is separated (with restriction enzyme digest, UV/chemical, or similar) and DNA side chain modifications, such as hairpins, are read out on nanopore generate a barcode signal to allow identification of SNP.

Example 7: Multi-Omics

Several multi-omics applications are possible using the assay-identification molecules of the present disclosure. As an example as illustrated in FIG. 14, the detection from the same sample of both cell surface protein expression, RNA-expression and DNA-detection (e.g. SNP) is shown.

A sample of cells is incubated with biotin-labelled assay-identification molecules whereby the assay molecules bind to target cell surface proteins. Next, the cells are washed to remove non-bound biotin-labelled assay-identification molecules. Proteinase K digestion results in cell killing and digestion through proteolysis and also results in proteolytic digestion of the assay molecules thereby separating the identification molecules from assay molecules. Next, spin column-based nucleic acid purification is used to isolate and purify from the sample simultaneously total RNA, genomic DNA (gDNA) and identification molecules. The purified total RNA and gDNA can be analyzed in a separate step using assay-identification molecules according to the methods described in this application. The identification molecules which were released from the assay-identification molecules bound to the cell surface can be captured on streptavidin coated magnetic beads.

The identification molecule is removed from the streptavidin coated magnetic beads with phenol (Bearden et al., 2020) or using a separation site (e.g. restriction enzyme). DNA side chain modifications, such as DNA hairpins, on the identification molecule are read out on the nanopore to generate a barcode signal, allowing for identification of target proteins.

Figure 14:
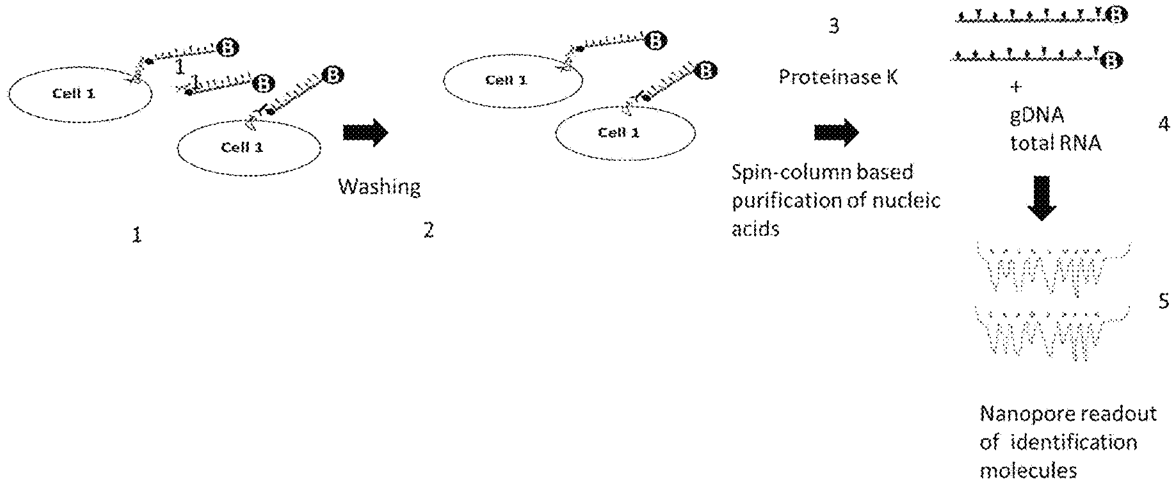
FIG. 14 illustrates an example of a multi-omics application according to an embodiment.

In step 1 of FIG. 14, cell surface proteins are labelled with biotin-labelled assay-identification molecules. In step 2, cells are washed to remove non-bound biotin-labelled assay-identification molecules. In step 3, proteinase K digestion separates identification molecules from assay molecules. In step 4, spin column-based nucleic acid purification is used to isolate simultaneously total RNA, gDNA and identification molecules from the sample. In step 5, purified total RNA and gDNA are analyzed using assay-identification molecules according to the methods described in the present disclosure. In step 6, the identification molecules which were released from the assay-identification molecules bound to the cell surface can be captured on streptavidin coated magnetic beads. The identification molecule is removed from the streptavidin coated magnetic beads with phenol (Bearden et al., 2020) or using a separation site (e.g. UV/chemical/restriction enzyme, etc.). DNA side chain modifications, such as DNA hairpins, are read out on nanopore to generate a barcode signal to allow identification of target protein.

Example 8: Spatial Omics Analysis

Figure 15:
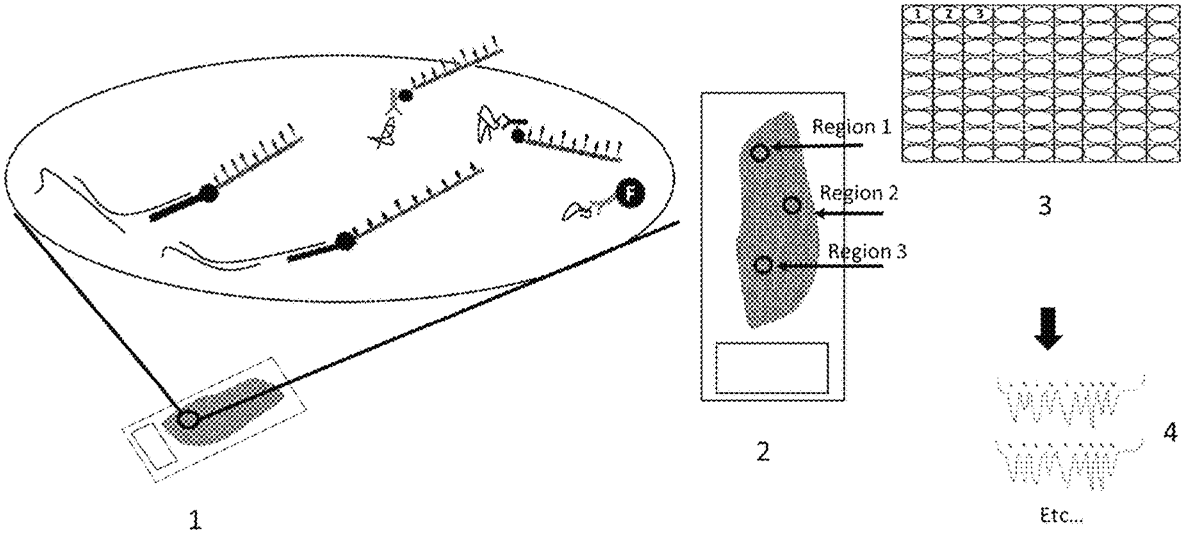
FIG. 15 illustrates an example of spatial omics analysis according to an embodiment.

For Spatial Omics analysis, as illustrated in FIG. 15, FFPE, fresh or fixed frozen tissue sections undergo standard tissue preparation to expose RNA and protein targets. Next, the tissue section is incubated with assay-identification molecules targeting RNA and proteins. The assay molecules are linked to the identification molecules using a UV-photocleavable linker. Fluorescent antibodies are also added for imaging the section and to identify regions of interest for spatial analysis. A region of interest in the tissue section is selectively illuminated with UV-light, which leads to separation of the identification molecules from the assay molecules. The slide is than washed to elute the identification molecules from the region of interest, and the eluate from a region of interest is stored in a well of a 96-well plate. This cycle is repeated for multiple regions of interest, whereby identification molecules from region 1 are captured in well 1, from region 2 in well 2 etc. Nanopore readout of the identification molecules from each well allows for identification of the presence of target proteins/RNA's in specific regions of interest.

It should be understood that this example may be extrapolated to other types of spatial omics analysis such as imaging-by-sequencing or DNA microscopy methods which use the proximity-dependent association between DNA molecules carrying random sequence identifiers (barcodes such as DNA side chain modifications) whereby readout or decoding of the random sequence identifiers is used to identify the network structure and spatial relationship between the DNA molecules.

In step 1 of FIG. 15, molecules in FFPE, fresh or fixed frozen tissue section undergoes standard tissue preparation to expose RNA and protein targets. Tissue section is incubated with assay-identification molecules targeting RNA and proteins. Fluorescent antibodies are also added for imaging the section. In step 2, a region of interest in the tissue section is selectively illuminated with UV-light to separate the identification molecules from the assay molecules. The slide is washed to elute the identification molecules from the region of interest in a well of a 96-well plate. In step 3, 3 Identification molecules from region 1 are captured in well 1, from region 2 in well 2, and so on. In step 4, nanopore readout of identification molecules from each well is performed.

ITEMIZED EMBODIMENTS

1. A method for detecting one or more target molecules in a sample using a nanopore sensor, the method comprising:
   providing (S1) at least one assay-identification molecule, wherein the assay-identification molecule comprises at least one identification molecule linked to an assay molecule, wherein the identification molecule is able to generate a unique identification signal when translocated through a nanopore sensor and wherein each assay molecule is able to bind to a target molecule of the one or more target molecules;
   incubating (S2) the at least one assay-identification molecule with a sample potentially comprising one or more target molecules, thereby allowing the at least one assay-identification molecule to bind to the one or more target molecules forming at least one target-assay-identification molecule, wherein the correlation between the unique identification signal of the identification molecule in the assay-identification molecule and the bound target molecule is known;
   removing (S3) any assay-identification molecule that has not bound any target molecule from the sample;
   separating (S4), in the remaining sample, the at least one identification molecule from the at least one target-assay-identification molecule;
   translocating (S5) the separated at least one identification molecule through a nanopore sensor to obtain at least one unique identification signal; and
   detecting (S6) any presence of the one or more target molecules in a sample by correlating the obtained at least one unique identification signal to the one or more target molecules.
2. The method according to item 1, wherein providing (S1) at least one assay-identification molecule comprises:
   providing (S11A) at least one identification molecule, wherein the identification molecule is able to generate a unique identification signal when translocated through a nanopore sensor; and
   linking (S12A) the at least one identification molecule to an assay molecule thereby forming at least one assay-identification molecule, wherein each assay molecule is able to bind to a target molecule of the one or more target molecules.
3. The method according to item 2, wherein the identification molecule has a backbone to which a plurality of modifications are added, and wherein generating (S11A) at least one identification molecule comprises:
   providing (S11A1) a backbone; and
   adding (S11A2) a plurality of modifications to said backbone to obtain an identification molecule.
4. The method according to item 1, wherein the identification molecule has a backbone to which a plurality of modifications are added, and wherein providing (S1) at least one assay-identification molecule comprises:

providing (S11B) at least one assay molecule, wherein each assay molecule is able to bind to a target molecule of the one or more target molecules;

generating (S12B) a backbone molecule linked to the assay molecule using rolling circle amplification;

adding (S13B) a plurality of backbone modifications to said at least one backbone molecule to obtain an identification molecule linked to the assay molecule, thereby obtaining least one assay-identification molecule.

5. The method according to item 4, wherein generating a backbone molecule linked to the assay molecule comprises:

adding (S12B1) at least one backbone template to the at least one assay molecule;

adding (S12B2) a polymerase to expand the at least one backbone template to obtain at least one backbone molecule;

6. The method according to any one of the preceding items, wherein separating (S4) the at least one identification molecule from the at least one target-assay-identification molecule comprises removing the identification molecule from the sample.

7. The method according to any one of the preceding items, wherein the identification molecule has a backbone to which a plurality of modifications are added, and wherein each modification give rise to a peak when translocated through the nanopore sensor.

8. The method according to item 7, wherein said modifications are selected from a plurality of modification types.

9. The method according to item 8, wherein each peak of the plurality of modifications is assigned an identification value, and wherein all the identification values of the corresponding modifications give rise to an array of identification values corresponding to the unique identification signal of the identification molecule.

10. The method according to item 9, wherein the identification values are assigned based on i) a distance between the modifications, or ii) the modification type of the modifications.

11. The method according to items 9-10, wherein the identification values are assigned based on i) a distance between peaks in a readout from the nanopore sensor, ii) a magnitude of the peaks in a readout from the nanopore sensor, or iii) the duration of the peak in a readout from the nanopore sensor.

12. The method according to items 10-11, wherein different modification types give rise to peaks of different magnitudes.

13. The method according to any one of the preceding items, wherein the unique identification signal is a barcode signal.

14. The method according to item 13, wherein the assigned identification value is a barcode value, and wherein all the barcode values of the corresponding backbone modifications give rise to an array of barcode values corresponding to the unique barcode signal of the dentification molecule.

15. The method according to item 14, wherein two modification types are used, and each peak of the two modification types is assigned a barcode value of "0" or "1", and wherein all the barcode values of the corresponding backbone modifications give rise to an array of binary barcode values corresponding to the unique barcode signal of the identification molecule.

16. The method according to any one of the preceding items, wherein at least one the identification molecule comprise a small fraction at each end that give rise to a predetermined array of barcode values for detecting the orientation of the identification molecule as it translocates through the nanopore.

17. The method according to any one of the preceding items, wherein the unique identification signal is based on a transition time for the identification molecule as it transitions through the nanopore sensor, or a length of the identification molecule.

18. The method according to items 3-17, wherein the one or more backbone modifications are selected from bulky DNA structures, such as DNA hairpin structures, cruciform DNA, DNA-origami, and quadruplex DNA, DNA-modifications, such as biotin, oligo, peptide, PNA, saccharide, or organic molecules, and differentiated DNA structures, such as ssDNA differentiated into ssDNA hybridized with oligos or poly-ethylene glycol moieties, or a combination thereof.

19. The method according to items 3-18, wherein the backbone is a biopolymer backbone.

20. The method according to item 19, wherein the biopolymer backbone is selected from DNA, RNA, peptides, and saccharides.

21. The method according to item any one or the preceding items, wherein the identification molecule comprise a DNA backbone having a plurality of backbone modifications in the form of dumbbell hairpins.

22. The method according to item 3, wherein the backbone is a synthetic polymer backbone.

23. The method according to item 22, wherein the synthetic polymer backbone is selected from polyesters, polyamides, rigid-rod polymers and modified polymers with carbon linker segments.

24. The method according to item 3, wherein the backbone is an uncharged molecule, which is selected from polyethers, such as polyethylene glycol, PEG, or variants thereof, or structures such as nanotubes or nanowires.

25. The method according to any one of the preceding items, wherein the at least one assay molecule is linked to the identification molecule using direct conjugation, affinity-based conjugation, hybridization, ionic interaction, or crosslinking, crosslinking including click chemistry.

26. The method according to any one of the preceding items, wherein each one of the at least one assay molecule is linked to more than one identification molecule.

27. The method according to any one of the preceding items, wherein the at least one assay molecules is selected from proteins, peptides, DNA, RNA, molecularly imprinted polymers, chemical compounds, metal ions, lipids, polysaccharides, vesicles, whole cells, and polystyrene beads.

28. The method according to item 27, wherein the assay molecule is an antibody or an aptamer.

29. The method according to any one of the preceding items, wherein the at least one identification molecule is separated from the target-assay-identification molecule by photolysis, heat, pH change, chemical removal or enzymatic removal.

30. The method according to any one of the preceding items, wherein the method is used for detecting the presence of one or more target molecules in a sample by detecting the unique identification signal associated with the target molecules in the nanopore sensor.

31. The method according to any one of the preceding items, wherein the method is used for quantifying one or more target molecules in a sample by detecting and quantifying the unique identification signal associated with the respective target in the nanopore sensor.

32. The method according to any one of the preceding items, wherein the sample is selected from biological samples and non-biological samples.

33. The method according to any one of the preceding items, wherein the sample is a biological sample such as biological fluids, including blood, serum, plasma, saliva and urine, cells, including cell populations and cell cultures, cell digests, and environmental samples.

34. The method according to any one of the preceding items, wherein the one or more target molecules are biomolecules.

35. The method according to item 34, wherein the one or more target biomolecules are selected from polypeptides, such as peptides and proteins, polynucleotides, such as DNA- or RNA-polymers, lipids, and polysaccharides.

36. The method according to any one of the preceding items, wherein the nanopore sensor comprises a solid state nanopore.

37. The method according to any one of the preceding items, wherein the nanopore sensor has a field effect transistor (FET) embedded in the nanopore.

38. A system for detecting and/or quantifying a target molecule in a sample, the system comprising:

a first electrolyte reservoir and a second electrolyte reservoir, the first and second reservoirs being separated by a barrier comprising a nanopore; and optionally, electrodes for translocating molecules through the nanopore from the first electrolyte reservoir to the second electrolyte reservoir, wherein at least one of the first and second electrolyte reservoirs comprises identification molecules, wherein the identification molecules are able to generate a unique identification signal when translocated through the nanopore.

39. The system according to item 38, wherein the diameter of the nanopore is adjusted to the diameter of the identification molecules.

40. The system according to items 38-39, wherein the system is used for carrying out the method of any one of items 1-37.

41. The system according to items 17-39, wherein the nanopore sensor has a field effect transistor (FET) embedded in the nanopore.

The invention claimed is:

1. A method for detecting one or more target molecules in a sample using a nanopore sensor, the method comprising:

providing at least one assay-identification molecule, wherein the at least one assay-identification molecule comprises at least one identification molecule linked to an assay molecule, wherein the at least one identification molecule is able to generate a unique identification signal when translocated through the nanopore sensor and wherein each assay molecule is able to bind to a target molecule of the one or more target molecules;

incubating the at least one assay-identification molecule with the sample potentially comprising the one or more target molecules, thereby allowing the at least one assay-identification molecule to bind to the one or more target molecules forming at least one target-assay-identification molecule, wherein a correlation between the unique identification signal of the assay-identification molecule and the at least one bound target molecule is known;

removing any assay-identification molecule that has not bound any target molecule from the sample;

separating the at least one identification molecule from the at least one target-assay-identification molecule;

translocating the separated at least one identification molecule through the nanopore sensor to obtain at least one unique identification signal; and detecting any presence of the one or more target molecules in the sample by correlating the obtained at least one unique identification signal to the one or more target molecules, wherein the at least one identification molecule has a backbone to which a plurality of modifications are added, said backbone being a double-stranded DNA (dsDNA), and wherein the nanopore sensor comprises a remote extended field effect transistor (FET), where an electrode wrapped around a nanopore of the nanopore senor is connected to a remote gate sensor of the remote extended FET.

2. The method according to claim 1, wherein the at least one identification molecule has a backbone to which a plurality of modifications are added, and wherein each modification gives rise to a peak when translocated through the nanopore sensor.

3. The method according to claim 1, wherein said modifications are selected from a plurality of modification types, and wherein each peak of the plurality of modifications is assigned an identification value, and wherein all the identification values of the corresponding modifications give rise to an array of identification values corresponding to the at least one unique identification signal of the at least one identification molecule.

4. The method according to claim 3, wherein the identification values are assigned based on i) a distance between the modifications, or ii) the modification type.

5. The method according to claim 3, wherein two modification types are used, and each peak of the two modification types is assigned an identification value of "0" or "1", and wherein all the identification values of the corresponding modifications give rise to an array of binary identification values corresponding to the at least one unique identification signal of the at least one identification molecule.

6. The method according to claim 1, wherein the at least one identification molecule comprises a small fraction at each end that gives rise to a predetermined array of identification values for detecting an orientation of the at least one identification molecule as it translocates through the nanopore sensor.

7. The method according to claim 1, wherein each one of the at least one assay molecule is linked to more than one identification molecule.

8. The method according to claim 1, wherein the at least one assay molecule is linked to the at least one identification molecule using direct conjugation, affinity-based conjugation, hybridization, ionic interaction, or crosslinking, crosslinking including click chemistry.

9. The method according to claim 1, wherein the at least one identification molecule is separated from the at least one target-assay-identification molecule by photolysis, heat, pH change, chemical removal or enzymatic removal.

10. The method according to claim 1, wherein the one or more backbone modifications are selected from:

bulky DNA structures comprising DNA hairpin structures, cruciform DNA, DNA-origami, quadruplex DNA, or a combination thereof, DNA-modifications comprising biotin, oligo, peptide, PNA, saccharide, organic molecules, or a combination thereof, and differentiated DNA structures comprising ssDNA differentiated into ssDNA hybridized with oligos or polyethylene glycol moieties, or a combination thereof.

11. The method according to claim 1, wherein the at least one assay molecule is selected from proteins, peptides, DNA, RNA, molecularly imprinted polymers, chemical compounds, metal ions, lipids, polysaccharides, vesicles, whole cells, polystyrene beads, an antibody, or an aptamer.

12. The method according to claim 1, wherein the nanopore sensor comprises a solid state nanopore.

13. The method according to claim 1, wherein the at least one unique identification signal is based on a transition time for the at least one identification molecule as it transitions through the nanopore sensor, and/or a length of the at least one identification molecule.

14. The method according to claim 1, wherein the method is used for detecting the presence of one or more target biomolecules in a biological sample by detecting specific barcodes associated with the one or more target biomolecules in the nanopore sensor, and/or for quantifying the one or more target biomolecules in the biological sample by detecting and quantifying the specific barcodes associated with the respective target biomolecule in the nanopore sensor.

* * * * *